US012661388B2

(12) United States Patent
Sangaralingham et al.

(10) Patent No.: US 12,661,388 B2
(45) Date of Patent: Jun. 23, 2026

(54) ASSESSING AND TREATING ACUTE DECOMPENSATED HEART FAILURE

(71) Applicant: Mayo Foundation for Medical Education and Research, Rochester, MN (US)

(72) Inventors: Sasantha J. Sangaralingham, Rochester, MN (US); Xiao Ma, Rochester, MN (US); John C. Burnett, Jr., Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 944 days.

(21) Appl. No.: 17/911,285

(22) PCT Filed: Mar. 12, 2021

(86) PCT No.: PCT/US2021/022168
§ 371 (c)(1),
(2) Date: Sep. 13, 2022

(87) PCT Pub. No.: WO2021/183928
PCT Pub. Date: Sep. 16, 2021

(65) Prior Publication Data
US 2023/0127487 A1 Apr. 27, 2023

Related U.S. Application Data

(60) Provisional application No. 62/989,315, filed on Mar. 13, 2020.

(51) Int. Cl.
| | |
|---|---|
| *A61K 35/34* | (2015.01) |
| *A61K 38/22* | (2006.01) |
| *A61P 43/00* | (2006.01) |
| *C07K 14/47* | (2006.01) |
| *G01N 33/53* | (2006.01) |
| *G01N 33/68* | (2006.01) |

(52) U.S. Cl.
CPC .......... *A61K 38/2242* (2013.01); *A61P 43/00* (2018.01); *G01N 33/6893* (2013.01); *G01N 2333/58* (2013.01); *G01N 2800/325* (2013.01)

(58) Field of Classification Search
CPC . A61K 38/2242; A61P 43/00; G01N 33/6893; G01N 2333/58; G01N 2800/325; G01N 2800/52; G01N 2800/56; C07K 14/58
See application file for complete search history.

(56) References Cited

U.S. PATENT DOCUMENTS

| | | | |
|---|---|---|---|
| 4,757,048 | A | 7/1988 | Lewicki et al. |
| 9,857,382 | B2 | 1/2018 | Sangaralingham et al. |
| 2010/0297021 | A1 | 11/2010 | Wendt et al. |
| 2011/0152194 | A1 | 6/2011 | Burnett, Jr. et al. |

| | | | |
|---|---|---|---|
| 2015/0005371 | A1* | 1/2015 | Ikeda .................. C07K 14/4705 |
| | | | 435/320.1 |
| 2015/0037359 | A1 | 2/2015 | Schellenberger et al. |
| 2015/0224174 | A1 | 8/2015 | Mitrovic et al. |
| 2015/0293119 | A1 | 10/2015 | Sangaralingham et al. |
| 2016/0252528 | A1 | 9/2016 | Sangaralingham et al. |
| 2022/0155322 | A1 | 5/2022 | Sangaralingham et al. |

FOREIGN PATENT DOCUMENTS

| | | |
|---|---|---|
| WO | WO 2009/149161 | 12/2009 |
| WO | WO 2013/095759 | 6/2013 |
| WO | WO 2013/103896 | 7/2013 |
| WO | WO 2020/190532 | 9/2020 |

OTHER PUBLICATIONS

Anavekar et al., "Relation between renal dysfunction and cardiovascular outcomes after myocardial infarction," N. Engl. J. Medicine, 351(13):1285-1295, Sep. 23, 2004.
Aviv et al., "Urinary neutral endopeptidase 24.11 activity: modulation by chronic salt loading," Kidney International, 47(3):855-860, Mar. 1995.
Burnett et al., "Atrial natriuretic peptide elevation in congestive heart failure in the human," Science, 231(4742):1145-1147, Mar. 1986.
Canaan-Kühl et al., "C-type natriuretic peptide inhibits mesangial cell proliferation and matrix accumulation in vivo," Kidney International, 53(5):1143-1151, May 1998.
Cataliotti et al., "CNP production in the kidney and effects of protein intake restriction in nephrotic syndrome," Am. J. Physiol. Renal Physiology, 283(3):F464-F472, Sep. 2002.
Chen et al., "C53: A novel particulate guanylyl cyclase B receptor activator that has sustained activity in vivo with anti-fibrotic actions in human cardiac and renal fibroblasts," J. Mol. Cell Cardiology, 130:140-150, Apr. 4, 2019.
Chen et al., "CRRL269: A Novel Particulate Guanylyl Cyclase A Receptor Peptide Activator for Acute Kidney Injury," Circ. Research, 124(10):1462-1472, May 10, 2019.
Chen et al., "C-type natriuretic peptide: the endothelial component of the natriuretic peptide system," J. Cardiovasc. Pharmacology, 32(Suppl 3):S22-S28, 1998.

(Continued)

*Primary Examiner* — Julie Ha
*Assistant Examiner* — Kristina M Hellman
(74) *Attorney, Agent, or Firm* — Fish & Richardson P.C.

(57) ABSTRACT

This document provides methods and materials involved in assessing mammals with acute decompensated heart failure (ADHF), as well as methods and materials involved in assessing outcomes. For example, methods and materials for using the level of plasma CNP and the level of urinary CNP to determine whether or not a mammal is developing or likely to develop more severe ADHF, as well as methods and materials for using the level of plasma CNP and the level of urinary CNP to identify patients having an increased likelihood of experiencing a poor outcome are provided.

2 Claims, 15 Drawing Sheets

Specification includes a Sequence Listing.

(56) References Cited

OTHER PUBLICATIONS

Chen et al., "Stabilization of Perivascular Mast Cells by Endothelial CNP (C-Type Natriuretic Peptide)," Arterioscler. Thromb. Vasc. Biology, 40(3):682-696, Jan. 2, 2020.

Damman et al., "Renal impairment, worsening renal function, and outcome in patients with heart failure: an updated meta-analysis," Eur. Heart Journal, 35(7):455-469, Oct. 27, 2013.

Del Ry et al. "C-type natriuretic peptide plasma levels increase in patients with chronic heart failure as a function of clinical severity" Eur. J. Heart Failure, 7(7):1145-1148, May 26, 2005.

D'Souza et al., "Autocrine and paracrine actions of natriuretic peptides in the heart," Pharmacol. Therapy, 101(2):113-129, Feb. 2004.

Furuya et al., "C-type natriuretic peptide inhibits intimal thickening after vascular injury," Ann. NY Acad. Sciences, 748(1):517-523, Jan. 17, 1995.

Go et al., "Acute kidney injury and risk of heart failure and atherosclerotic events," Clin. J. Am. Soc. Nephrology, 13(6):833-841, Jun. 7, 2018.

Gülberg et al., "Increased renal production of C-type natriuretic peptide (CNP) in patients with cirrhosis and functional renal failure," Gut, 47(6):852-857, Dec. 2000.

Horio et al., "Gene expression, secretion, and autocrine action of C-type natriuretic peptide in cultured adult rat cardiac fibroblasts," Endocrinology, 144(6):2279-2284, Jun. 2003.

Ichiki et al., "Cardiac fibrosis in end-stage human heart failure and the cardiac natriuretic peptide guanylyl cyclase system: regulation and therapeutic implications," J. Mol. Cell Cardiology, 75:199-205, Aug. 9, 2014.

Ichiki et al., "Natriuretic peptide based therapeutics for heart failure: Cenderitide: A novel first-in-class designer natriuretic peptide," Int. J. Cardiology, 281:166-171, Apr. 15, 2019.

International Preliminary Report on Patentability in International Appln. No. PCT/US2021/022168, mailed on Sep. 22, 2022, 11 pages.

International Search Report and Written Opinion in International Appln. No. PCT/US2021/022168, mailed on Jul. 26, 2021, 14 pages.

Kalra et al., "C-type natriuretic peptide production by the human kidney is blunted in chronic heart failure," Clin. Sci. (London), 118(1):71-77, Oct. 2, 2009.

Kalra et al., "Myocardial production of C-type natriuretic peptide in chronic heart failure," Circulation, 107(4):571-573, Feb. 4, 2003.

Kawakami et al., "A Human Study to Evaluate Safety, Tolerability, and Cyclic GMP Activating Properties of Cenderitide in Subjects With Stable Chronic Heart Failure," Clin. Pharmacol. Therapy, 104(3):546-552, Jan. 11, 2018.

Knecht et al., "Increased expression of renal neutral endopeptidase in severe heart failure," Life Sciences, 71(23):2701-2712, Oct. 25, 2002.

Komatsu et al., "C-Type Natriuretic Peptide (CNP) in Rats and Humans," Endocrinology, 129(2):1104-1106, Aug. 1991.

Langenickel et al., "Cardiac hypertrophy in transgenic rats expressing a dominant-negative mutant of the natriuretic peptide receptor B," Proc. Natl. Acad. Sci. USA, 103(12):4735-4740, Mar. 14, 2006.

Lok et al., "Prognostic value of N-terminal pro C-type natriuretic peptide in heart failure patients with preserved and reduced ejection fraction," Eur. J. Heart Failure, 16(9):958-966, Jul. 31, 2014.

Ma et al., "Plasma and Urinary C-Type Natriuretic Peptide as Prognostic Biomarkers for Human Acute Decompensated Heart Failure," J. Am. Coll. Cardiology, 75(11S1):918, Mar. 16, 2020.

Ma et al., "Prognostic Value of Urinary and Plasma C-Type Natriuretic Peptide in Acute Decompensated Heart Failure," JACC: Heart Failure, Jul. 7, 2021, 9(9):613-623.

Mahmood et al., "The epidemiology of congestive heart failure: the Framingham Heart Study perspective," Glob. Heart, 8(1):77-82, Mar. 1, 2013.

Manzano-Fernandez et al., "Impact of kidney dysfunction on plasma and urinary N-terminal pro-B-type natriuretic peptide in patients with acute heart failure," Congest. Heart Failure, 16(5):214-220, Apr. 28, 2010.

Martin et al., "Abstract 1484: New Insights into the Kidney-Heart Connection: Mild Renal Insufficiency Induces Cardiac Fibrosis and Diastolic Dysfunction Followed by Late Systolic Impairment," Circulation, 118:S_334-S 335, Oct. 28, 2008, 1 page.

Mattingly et al., "Presence of C-type natriuretic peptide in human kidney and urine," Kidney International, 46(3):744-747, Sep. 1994.

Mentz et al., "Pathophysiology and clinical evaluation of acute heart failure," Nat. Rev. Cardiology, 13(1):28-35, Sep. 15, 2015.

Moyes et al., "C-type natriuretic peptide co-ordinates cardiac structure and function," Eur. Heart Journal, 41(9):1006-1020, Mar. 1, 2020.

Moyes et al., "C-type Natriuretic Peptide: A Multifaceted Paracrine Regulator in the Heart and Vasculature," Int. J. Mol. Sciences, 20(9):2281, May 8, 2019, 23 pages.

Mullens et al., "Evaluation of kidney function throughout the heart failure trajectory—a position statement from the Heart Failure Association of the European Society of Cardiology," Eur. J. Heart Failure, 22(4):584-603, Jan. 7, 2020.

Nakao et al., "Endothelium-Derived C-Type Natriuretic Peptide Contributes to Blood Pressure Regulation by Maintaining Endothelial Integrity," Hypertension, 69(2):286-296, Jan. 3, 2017.

Nazario et al., "Atrial and brain natriuretic peptides stimulate the production and secretion of C-type natriuretic peptide from bovine aortic endothelial cells," J. Clin. Investigation, 95(3):1151-1157, Mar. 1995.

Ng et al., "Diagnosis of heart failure using urinary natriuretic peptides" Clin. Sci. (London), 106(2):129-133, Feb. 2004.

Palmer et al., "Regional release and clearance of C-type natriuretic peptides in the human circulation and relation to cardiac function," Hypertension, 54(3):612-618, Jul. 20, 2009.

Peterson et al., "A validated risk score for in-hospital mortality in patients with heart failure from the American Heart Association get with the guidelines program," Circ. Cardiovasc. Qual. Outcomes, 3(1):25-32, Dec. 8, 2009.

Prickett et al., "Urinary Amino-Terminal Pro-C-Type Natriuretic Peptide: A Novel Marker of Chronic Kidney Disease in Diabetes," Clin. Chemistry, 65(10):1248-1257, Oct. 1, 2019.

Reginauld et al., "Differential Regulation of ANP and BNP in Acute Decompensated Heart Failure: Deficiency of Anp," Jacc Heart Failure, 7(10):891-898, Sep. 11, 2019.

Richards et al., "Plasma N-terminal pro-brain natriuretic peptide and adrenomedullin: new neurohormonal predictors of left ventricular function and prognosis after myocardial infarction," Circulation, 97(19):1921-1929, May 19, 1998.

Sangaralingham et al., "Circulating C-type natriuretic peptide and its relationship to cardiovascular disease in the general population," Hypertension, 65(6):1187-1194, Apr. 20, 2015.

Sangaralingham et al., "The aging heart, myocardial fibrosis, and its relationship to circulating C-type natriuretic peptide," Hypertension, 57(2):201-207, Dec. 28, 2010.

Sangaralingham et al., "Urinary C-type natriuretic peptide excretion: a potential novel biomarker for renal fibrosis during aging," Am. J. Physiol. Renal Physiology, 301(5):F943-F952, Nov. 2011.

Soeki et al., "C-type natriuretic peptide, a novel antifibrotic and antihypertrophic agent, prevents cardiac remodeling after myocardial infarction," J. Am. Coll. Cardiology, 45(4):608-616, Feb. 15, 2005.

Spiranec et al., "Endothelial C-Type Natriuretic Peptide Acts on Pericytes to Regulate Microcirculatory Flow and Blood Pressure," Circulation, 138(5):494-508, Jul. 31, 2018.

Stingo et al., "Presence of C-type natriuretic peptide in cultured human endothelial cells and plasma," Am. J. Physiology, 263(4 Pt 2):H1318-H1321, Oct. 1992.

Suga et al., "Cytokine-induced C-type natriuretic peptide (CNP) secretion from vascular endothelial cells-evidence for CNP as a novel autocrine/paracrine regulator from endothelial cells," Endocrinology, 133(6):3038-3041, Dec. 1993.

Vaduganathan et al., "Relation of serum and urine renal biomarkers to cardiovascular risk in patients with type 2 diabetes mellitus and

(56)             References Cited

OTHER PUBLICATIONS recent acute coronary syndromes (from the EXAMINE Trial)," Am. J. Cardiology, 123(3):382-391, Nov. 6, 2018.

Volpe et al., "Natriuretic peptides in cardiovascular diseases: current use and perspectives," Eur. Heart Journal, 35(7):419-425, Feb. 14, 2014.

Wang et al., "Cardiomyocyte-restricted over-expression of C-type natriuretic peptide prevents cardiac hypertrophy induced by myocardial infarction in mice," Eur. J. Heart Failure, 9(6-7):548-557, Apr. 3, 2007.

Wei et al., "Action of C-type natriuretic peptide in isolated canine arteries and veins," Am. J. Physiology, 264(1 Pt 2):H71-H73, Jan. 1993.

Wright et al., "Amino-terminal pro-C-type natriuretic peptide in heart failure," Hypertension, 43(1):94-100, Dec. 1, 2003.

Zakeri et al., "Abstract 13451: Renal Derived Amino-Terminal C-Type Natriuretic Peptide-53 is a Novel Urinary Biomarker Which Predicts Adverse Outcomes in Patients with Acute Decompensated Heart Failure," Circulation, 126(S21):A13451, Mar. 28, 2018, 5 pages.

Zakeri et al., "Urinary C-type natriuretic peptide: a new heart failure biomarker," JACC Heart Failure, 1(2):170-177, Apr. 2013.

Zakeri et al., "Urinary C-type natriuretic peptide: an emerging biomarker for heart failure and renal remodeling," Clin. Chim. Acta, 443:108-113, Mar. 30, 2015.

Extended European Search Report in European Appln. No. 21768083. 4, dated Mar. 28, 2024, 10 pages.

* cited by examiner

☒ Normal pCNP/Normal uCNP

☐ Elevated pCNP/Normal uCNP

■ Normal pCNP/Elevated uCNP

☐ Elevated pCNP/Elevated uCNP

| | | | |
|---|---|---|---|
| 100 (51) | 61 (29) | 51 (23) | 40 (18) |
| 100 (19) | 33 (6) | 22 (4) | 17 (3) |
| 100 (91) | 44 (37) | 32 (27) | 21 (17) |
| 100 (47) | 37 (17) | 20 (9) | 13 (6) |

⋯⋯ Normal pCNP/Normal uCNP     ‑ ‑ Normal pCNP/Elevated uCNP

⋯⋯ Elevated pCNP/Normal uCNP     — Elevated pCNP/Elevated uCNP

| | | | |
|---|---|---|---|
| 100 (51) | 65 (23) | 59 (20) | 47 (16) |
| 100 (19) | 39 (6) | 32 (4) | 24 (3) |
| 100 (91) | 48 (31) | 39 (24) | 29 (16) |
| 100 (47) | 39 (14) | 20 (7) | 17 (5) |

⋯⋯  Normal pCNP/Normal uCNP          ─ ─  Normal pCNP/Elevated uCNP

⋯⋯  Elevated pCNP/Normal uCNP          ──  Elevated pCNP/Elevated uCNP

FIG. 7A          FIG. 7B
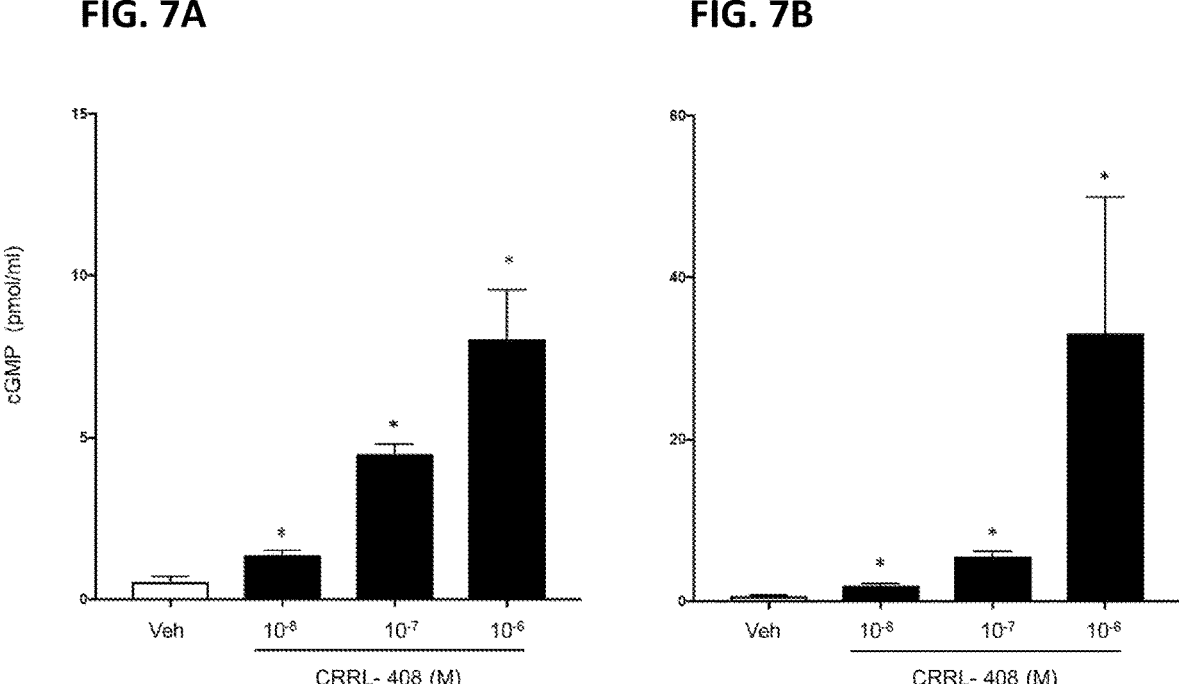

FIG. 8A                    FIG. 8B
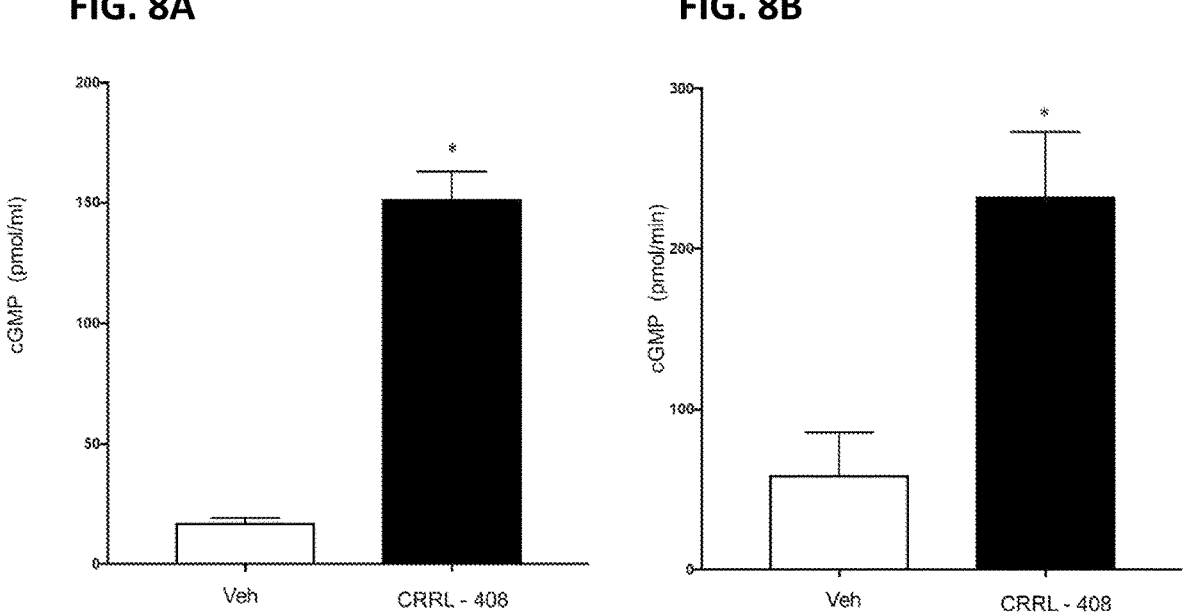

ASSESSING AND TREATING ACUTE DECOMPENSATED HEART FAILURE

CROSS-REFERENCE TO RELATED APPLICATIONS

This application is a National Stage application under 35 U.S.C. § 371 of International Application No. PCT/US2021/022168 having an International Filing Date of Mar. 12, 2021, which claims priority from U.S. Provisional Application Ser. No. 62/989,315, filed Mar. 13, 2020. The disclosures of the prior applications are considered part of (and are incorporated by reference in) the disclosure of this application.

STATEMENT AS TO FEDERALLY SPONSORED RESEARCH

This invention was made with government support under HL132854 awarded by the National Institutes of Health. The government has certain rights in the invention.

SEQUENCE LISTING

This application contains a Sequence Listing that has been submitted electronically as an ASCII text file named 07039_1962WO1_ST25.txt. The ASCII text file, created on Mar. 11, 2021, is 24,621 bytes in size. The material in the ASCII text file is hereby incorporated by reference in its entirety.

BACKGROUND

1. Technical Field

This document relates to methods and materials involved assessing and treating heart, renal, or cardiorenal conditions (e.g., acute decompensated heart failure (ADHF)). For example, this document provides methods and materials for using the level of plasma C-type natriuretic peptide (CNP) and the level of urinary CNP to determine whether or not a mammal with ADHF is at risk of a poor outcome or greater severity of disease. This document also provides natriuretic peptides and methods and materials for using natriuretic peptides to treat conditions such as ADHF.

2. Background Information

CNP is part of the natriuretic peptide family, is produced in the kidney and the endothelium, and can be detected in the plasma and urine. CNP is synthesized as a precursor 103 amino acid (AA) protein, proCNP, which is then cleaved into NT-proCNP (AA 1-50) and CNP-53 (AA 51-103) by the intracellular endoprotease furin. Additional downstream processing by an unknown enzyme cleaves CNP-53, giving rise to the primary biologically active form, CNP-22 (AA 82-103) and an amino-terminal fragment, NT-CNP-53 (AA 51-81).

CNP has potent anti-fibrotic and anti-proliferative properties through the activation of the natriuretic peptide receptor B (NPR-B), otherwise known as guanylyl cyclase receptor B (GC-B), and the generation of the second messenger 3',5'-cyclic guanosine monophosphate (cGMP). CNP has limited natriuretic and diuretic actions.

SUMMARY

This document provides methods and materials for assessing mammals with heart, renal, or cardiorenal conditions (e.g., ADHF), and determining whether they are at risk of more severe effects (e.g., ADHF effects) and/or poor outcomes. For example, this document provides methods and materials for using the level of plasma CNP and the level of urinary CNP to determine whether or not a mammal (e.g., a human) is developing or is likely to experience a poor outcome, such as rehospitalization or rehospitalization and death. Determining if a mammal (e.g., a human) is likely to develop more severe effects of ADHF or a poor outcome by assessing the level of plasma CNP and the level of urinary CNP can aid in the identification of mammals (e.g., humans) that should be treated in a particular manner (e.g., by administering a natriuretic peptide such as CD-NP or a natriuretic peptide described herein) prior to the onset of more severe ADHF, thereby allowing for the initiation of strategies designed to slow or prevent the progression of ADHF to a poor outcome. CD-NP is a polypeptide with the following amino acid sequence: GLSKGCFGLKLDRI-GSMSGLGCPSLRDPRPNAP STSA (SEQ ID NO:1). The ability to identify patients as having an increased likelihood of experiencing a poor outcome based at least in part on an elevated level of plasma CNP and on an elevated level of urinary CNP can aid physicians and patients in making proper treatment decisions.

In general, one aspect of this document features methods for identifying a mammal having ADHF as being more or less likely to experience a severe effect of the ADHF. The methods can include, or consist essentially of, determining whether or not the mammal contains the presence of an elevated level of plasma CNP and an elevated level of urinary CNP, and identifying the mammal as being more likely to experience the severe effect when the mammal contains the elevated level of plasma CNP and the elevated level of urinary CNP, or identifying the mammal as being less likely to experience the severe effect when the mammal does not contain the elevated level of plasma CNP and the elevated level of urinary CNP. The mammal can be a human. The elevated level of the plasma CNP can be a level that is greater than 24.7 pg/mL. The elevated level of the urinary CNP can be a level that is greater than 33.1 ng/g of creatinine (cr). The severe effect can be severe cardiac dysfunction, reduced estimated glomerular filtration rate (eGFR), atrial fibrillation, rehospitalization for ADHF, or rehospitalization and death from ADHF.

In another aspect, this document features methods for assessing a mammal identified as having ADHF. The methods can include, or consist essentially of, (a) detecting the presence of an elevated level of plasma CNP and an elevated level of urinary CNP in the mammal, and (b) classifying the mammal as being likely to experience severe effects of the ADHF based at least in part on the presence. The mammal can be a human. The elevated level of the plasma CNP can be a level that is greater than 24.7 pg/mL. The elevated level of the urinary CNP can be a level that is greater than 33.1 ng/g of cr. The severe effect can be severe cardiac dysfunction, reduced eGFR, atrial fibrillation, rehospitalization for ADHF, or rehospitalization and death from ADHF.

In another aspect, this document features methods for assessing an outcome for ADHF. The methods can include, or consist essentially of, determining whether or not a mammal having experienced ADHF contains the presence of an elevated level of plasma CNP and an elevated level of urinary CNP, and identifying the mammal as being likely where to experience a poor outcome when the mammal contains the elevated level of plasma CNP and the elevated level of urinary CNP, or identifying the mammal as not being likely to experience the poor outcome when the mammal does not contain the elevated level of plasma CNP and the elevated level of urinary CNP. The mammal can be a human. The elevated level of the plasma CNP can be a level that is greater than 24.7 pg/mL. The elevated level of the urinary CNP can be a level that is greater than 33.1 ng/g of cr. The poor outcome can be (a) rehospitalization (for ADHF or any other cause) or (b) rehospitalization and death (from ADHF or any other cause).

In another aspect, this document features methods for assessing an outcome for ADHF. The methods can include, or consist essentially of, (a) detecting the presence of an elevated level of plasma CNP and an elevated level of urinary CNP in a mammal having experienced ADHF, and (b) classifying the mammal as likely to experience a poor outcome based at least in part on the presence of the elevated levels. The mammal can be a human. The elevated level of the plasma CNP can be a level that is greater than 24.7 pg/mL. The elevated level of the urinary CNP can be a level that is greater than 33.1 ng/g of cr. The poor outcome can be (a) rehospitalization (for ADHF or any other cause) or (b) rehospitalization and death (from ADHF or any other cause).

In another aspect, this document features methods for assessing a mammal identified as having ADHF. The methods can include, or consist essentially of, (a) performing an immunoassay with an anti-CNP antibody to detect the presence of an elevated level of plasma CNP and an elevated level of urinary CNP in the mammal, and (b) classifying the mammal as being likely to experience severe effects of the ADHF based at least in part on the detected elevated level of plasma CNP and elevated level of urinary CNP. The mammal can be a human. The elevated level of the plasma CNP can be a level that is greater than 24.7 pg/mL. The elevated level of the urinary CNP can be a level that is greater than 33.1 ng/g of cr.

In another aspect, this document features methods for assessing an outcome for ADHF. The methods can include, or consist essentially of, (a) performing an immunoassay with an anti-CNP antibody to detect the presence of an elevated level of plasma CNP and an elevated level of urinary CNP in a mammal having ADHF, and (b) classifying the mammal as likely to experience a poor outcome based at least in part on the detected elevated level of plasma CNP and elevated level of urinary CNP. The mammal can be a human. The elevated level of the plasma CNP can be a level that is greater than 24.7 pg/mL. The elevated level of the urinary CNP can be a level that is greater than 33.1 ng/g of cr. The poor outcome can be (a) rehospitalization (for ADHF or any other cause) or (b) rehospitalization and death (from ADHF or any other cause).

In another aspect, this document features methods for treating a mammal having an increased risk of a poor ADHF outcome. The methods can include, or consist essentially of, (a) identifying the mammal as having the presence of an elevated level of plasma CNP and an elevated level of urinary CNP, and (b) administering, to the mammal, or instructing the mammal to self-administer, a composition including one or more natriuretic peptides to reduce the risk of the poor ADHF outcome. The mammal can be a human. The elevated level of the plasma CNP can be a level that is greater than 24.7 pg/mL. The elevated level of the urinary CNP can be a level that is greater than 33.1 ng/g of cr. The poor outcome can be (a) rehospitalization or (b) rehospitalization and death. The composition can include CD-NP. The composition can include a natriuretic peptide comprising the amino acid sequence set forth in SEQ ID NO:7, 8, 9, or 10. The composition can include a natriuretic peptide comprising the amino acid sequence set forth in SEQ ID NO:7 with zero, one, two, three, four, five, six, seven, eight, nine, or ten amino acid additions, deletions, or substitutions provided that the two cysteine residues are maintained and are the only two cysteine residues of said natriuretic peptide. The composition can include a natriuretic peptide comprising the amino acid sequence set forth in SEQ ID NO:8 with zero, one, two, three, four, five, six, seven, eight, nine, or ten amino acid additions, deletions, or substitutions provided that the two cysteine residues are maintained and are the only two cysteine residues of said natriuretic peptide. The composition can include a natriuretic peptide comprising the amino acid sequence set forth in SEQ ID NO:9 with zero, one, two, three, four, five, six, seven, eight, nine, or ten amino acid additions, deletions, or substitutions provided that the two cysteine residues are maintained and are the only two cysteine residues of said natriuretic peptide. The composition can include a natriuretic peptide comprising the amino acid sequence set forth in SEQ ID NO:10 with zero, one, two, three, four, five, six, seven, eight, nine, or ten amino acid additions, deletions, or substitutions provided that the two cysteine residues are maintained and are the only two cysteine residues of said natriuretic peptide. The method can include administering, to the mammal, or instructing the mammal to self-administer, an ACE inhibitor, an angiotensin receptor blocker, an aldosterone antagonist, or a statin.

In another aspect, this document features methods for treating ADHF. The methods can include, or consist essentially of, administering a composition to a mammal identified as having the presence of an elevated level of plasma CNP and an elevated level of urinary CNP, or instructing the mammal to self-administer the composition, where the composition includes one or more natriuretic peptides, and where the risk of a poor ADHF outcome is reduced. The mammal can be a human. The elevated level of the plasma CNP can be a level that is greater than 24.7 pg/mL. The elevated level of the urinary CNP can be a level that is greater than 33.1 ng/g of cr. The poor outcome can be (a) rehospitalization or (b) rehospitalization and death. The composition can include CD-NP. The composition can include a natriuretic peptide comprising the amino acid sequence set forth in SEQ ID NO:7, 8, 9, or 10. The composition can include a natriuretic peptide comprising the amino acid sequence set forth in SEQ ID NO:7 with zero, one, two, three, four, five, six, seven, eight, nine, or ten amino acid additions, deletions, or substitutions provided that the two cysteine residues are maintained and are the only two cysteine residues of said natriuretic peptide. The composition can include a natriuretic peptide comprising the amino acid sequence set forth in SEQ ID NO:8 with zero, one, two, three, four, five, six, seven, eight, nine, or ten amino acid additions, deletions, or substitutions provided that the two cysteine residues are maintained and are the only two cysteine residues of said natriuretic peptide. The composition can include a natriuretic peptide comprising the amino acid sequence set forth in SEQ ID NO:9 with zero, one, two, three, four, five, six, seven, eight, nine, or ten amino acid additions, deletions, or substitutions provided that the two cysteine residues are maintained and are the only two cysteine residues of said natriuretic peptide. The composition can include a natriuretic peptide comprising the amino acid sequence set forth in SEQ ID NO:10 with zero, one, two, three, four, five, six, seven, eight, nine, or ten amino acid additions, deletions, or substitutions provided that the two cysteine residues are maintained and are the only two cysteine residues of said natriuretic peptide.

In another aspect, this document features a polypeptide including the amino acid sequence set forth in SEQ ID NO:7, 8, 9, or 10.

In another aspect, this document features a composition including a polypeptide comprising the amino acid sequence set forth in SEQ ID NO:7, 8, 9, or 10.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 2B), and plasma CNP (FIG. 2C) in ADHF patients with left ventricular ejection fraction (LVEF)≤40% (HF with reduced EF) and LVEF>40% (HF with preserved EF). The P values shown were adjusted for age, sex, and BMI.

FIGS. 7A-7B are graphs plotting the level of cGMP generated in human renal fibroblasts (FIG. 7A) and human renal proximal tubular cells (FIG. 7B) treated with CRRL-408 (SEQ ID NO:10) at concentrations of $10^{-8}$, $10^{-7}$ or $10^{-6}$ M. Treatment buffer served as vehicle. *P<0.05 vs vehicle.

FIGS. 8A-8B are graphs plotting in vivo plasma (FIG. 8A) and urinary (FIG. 8B) cGMP levels in normal rats intravenously infused with CRRL-408 (SEQ ID NO:10) at a dose of 2.12 μg/kg/min in normal rats (N=4/group) and normal saline served as vehicle. * P<0.05 vs vehicle.

DETAILED DESCRIPTION

Figure 1A:
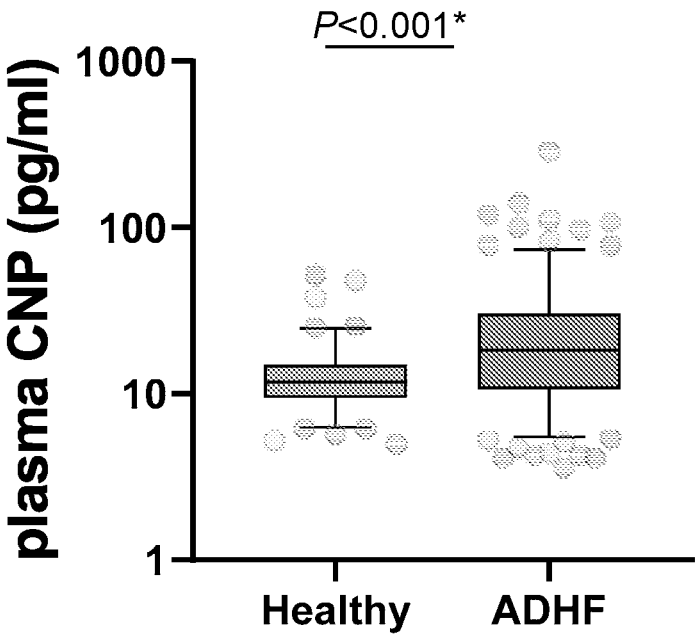
FIG. 1A is a graph plotting plasma CNP levels in healthy subjects and ADHF patients.

This document provides methods and materials involved in assessing and treating mammals having a heart, renal, or cardiorenal condition. Examples of heart, renal, and cardiorenal conditions that can be assessed and/or treated as described herein include, without limitation, ADHF, acute coronary syndromes, ventricular remodeling post-myocardial infarction, diabetic cardiomyopathy, cardiorenal syndrome, perioperative renal dysfunction, renal dysfunction secondary to heart failure, and diabetic nephropathy. For example, this document provides methods and materials for using the level of plasma CNP and the level of urinary CNP to determine whether or not a mammal is developing or is likely to develop more severe effects of ADHF. As described herein, the presence of an elevated level of plasma CNP and an elevated level of urinary CNP can indicate that the mammal is developing or is likely to develop more severe ADHF effects and/or is likely to experience a poor outcome. Examples of poor outcomes include, without limitation, rehospitalization, and rehospitalization and death. The methods and materials provided herein can be used to assess ADHF in any appropriate mammal including, without limitation, humans, monkeys, horses, cows, sheep, goats, mice, and rats.

The amino acid sequences of five molecular forms of human CNP are as follows:

```
Pro-CNP:
                                          (SEQ ID NO: 2)
KPGAPPKVPRTPPAEELAEPQAAGGGQKKGDKAPGGGGANLKGDRSRLL

RDLRVDTKSRAAWARLLQEHPNARKYKGANKKGLSKGCFGLKLDRIGSM

SGLGC;

NT-Pro-CNP₁₋₅₀:
                                          (SEQ ID NO: 3)
KPGAPPKVPRTPPAEELAEPQAAGGGQKKGDKAPGGGGANLKGDRSRLL

R;

CNP-53:
                                          (SEQ ID NO: 4)
DLRVDTKSRAAWARLLQEHPNARKYKGANKKGLSKGCFG

LKLDRIGSMSGLGC;

NT-CNP-53:
                                          (SEQ ID NO: 5)
DLRVDTKSRAAWARLLQEHPNARKYKGANKK; and CNP-22:
                                          (SEQ ID NO: 6)
GLSKGCFGLKLDRIGSMSGLGC.
```

The term "elevated level" as used herein with respect to plasma levels of CNP (or a particular molecular form of CNP such as CNP-53 or CNP-22) refers to any level that is above a threshold plasma level for a control population of healthy mammals (e.g., an age-matched random population of 10, 20, 30, 40, 50, 100, or 500 healthy mammals) that do not have ADHF. The term "elevated level" as used herein with respect to urinary levels of CNP (or a particular molecular form of CNP such as CNP-53 or CNP-22) refers to any level that is above a threshold urinary level for a control population of healthy mammals (e.g., an age-matched random population of 10, 20, 30, 40, 50, 100, or 500 healthy mammals) that do not have ADHF. In some cases, an elevated level of plasma CNP can be any level that is greater than 24.7 pg/mL. In some cases, an elevated level of urinary CNP can be any level that is greater than 33.1 ng/g cr.

Any appropriate method can be used to determine a plasma CNP level and a urinary CNP level. For example, polypeptide detection methods such as immunoassays (e.g., ELISAs or radioimmunoassays) and mass spectrometry can be used to determine the level of CNP in a plasma or urine sample. In some cases, radioimmunoassays can be used to determine the urinary CNP to plasma CNP ratio or the plasma CNP to urinary CNP ratio.

This document also provides methods and materials involved in assessing outcomes. For example, this document provides methods and materials for using the level of plasma CNP and the level of urinary CNP to determine whether or not a mammal is likely to experience a poor outcome. As described herein, the presence of an elevated level of plasma CNP and an elevated level of urinary CNP can indicate that the mammal is likely to experience a poor outcome. Examples of poor outcomes include, without limitation, rehospitalization, death, and rehospitalization with subsequent death. The methods and materials provided herein can be used to assess outcomes in any appropriate mammal including, without limitation, humans, monkeys, horses, cows, sheep, goats, rats, and mice.

This document also provides methods and materials to assist medical or research professionals in determining whether or not a mammal is developing or is likely to develop more severe effects of ADHF, as well as methods and materials to assist medical or research professionals in determining whether or not a mammal is likely to experience a poor outcome from ADHF. Medical professionals can be, for example, doctors, nurses, medical laboratory technologists, and pharmacists. Research professionals can be, for example, principal investigators, research technicians, postdoctoral trainees, and graduate students. A professional can be assisted in determining whether or not a mammal is developing or is likely to develop more severe effects of ADHF by (1) determining a plasma CNP level and a urinary CNP level, and (2) communicating information about those levels to that professional. A professional can be assisted in determining whether or not a mammal is likely to experience a poor outcome by (1) determining a plasma CNP level and a urinary CNP level, and (2) communicating information about that level to that professional.

Any method can be used to communicate information to another person (e.g., a professional). For example, information can be given directly or indirectly to a professional. In addition, any type of communication can be used to communicate the information. For example, mail, e-mail, telephone, and face-to-face interactions can be used. The information also can be communicated to a professional by making that information electronically available to the professional. For example, the information can be communicated to a professional by placing the information on a computer database such that the professional can access the information. In addition, the information can be communicated to a hospital, clinic, or research facility serving as an agent for the professional.

This document also provides natriuretic peptides and composition comprising one or more natriuretic peptides provided herein. For example, in one embodiment, this document provides natriuretic peptides having the amino acid sequence set forth in SEQ ID NO:7 or having the amino acid sequence set forth in SEQ ID NO:7 with one to ten (e.g., one, two, three, four, five, six, seven, eight, nine, or ten) amino acid additions, deletions, or substitutions provided that the two cysteine residues are maintained and are the only two cysteine residues of the natriuretic peptide. Examples of such natriuretic peptides include, without limitation, those set forth in Table 1.

In another embodiment, this document provides natriuretic peptides having the amino acid sequence set forth in SEQ ID NO:8 or having the amino acid sequence set forth in SEQ ID NO:8 with one to ten (e.g., one, two, three, four, five, six, seven, eight, nine, or ten) amino acid additions, deletions, or substitutions provided that the two cysteine residues are maintained and are the only two cysteine residues of the natriuretic peptide. Examples of such natriuretic peptides include, without limitation, those set forth in Table 2.

In another embodiment, this document provides natriuretic peptides having the amino acid sequence set forth in SEQ ID NO:9 or having the amino acid sequence set forth in SEQ ID NO:9 with one to ten (e.g., one, two, three, four, five, six, seven, eight, nine, or ten) amino acid additions, deletions, or substitutions provided that the two cysteine residues are maintained and are the only two cysteine residues of the natriuretic peptide. Examples of such natriuretic peptides include, without limitation, those set forth in Table 3.

In another embodiment, this document provides natriuretic peptides having the amino acid sequence set forth in SEQ ID NO:10 or having the amino acid sequence set forth in SEQ ID NO:10 with one to ten (e.g., one, two, three, four, five, six, seven, eight, nine, or ten) amino acid additions, deletions, or substitutions provided that the two cysteine residues are maintained and are the only two cysteine residues of the natriuretic peptide. Examples of such natriuretic peptides include, without limitation, those set forth in Table 4.

TABLE 1

Exemplary natriuretic peptides

| Natriuretic peptides | SEQ ID NO: |
|---|---|
| KKGLSKGCFGLKLDRIGSMSGLGCPSLRDPRPNAPSTSA | 7 |
| KKGLGCFGLKLDRIGSMSGLGCPSLRDPRPNAPSTSA | 11 |
| KKGLSKGCFGLKLDRIGSMSGLGCSLRDPRPNAPSTSA | 12 |
| KKGLGCFGLKLDRIGSMSGLGCSLRDPRPNAPSTSA | 13 |
| KKGLRKGCFGLKLDRIGSMSGLGCPSLRDPRPNAPSTSA | 14 |
| KKGLDKGCFGLKLDRIGSMSGLGCPSLRDPRPNAPSTSA | 15 |
| KKGLSDGCFGLKLDRIGSMSGLGCPSLRDPRPNAPSTSA | 16 |
| KKGLSGGCFGLKLDRIGSMSGLGCPSLRDPRPNAPSTSA | 17 |
| KKGLSKGCFGLKLDRIGSMSGLGCPSLRDPRPNAPSTSA | 18 |
| KKGLSKGCFGLKLDRIGSMSGLGCDSLRDPRPNAPSTSA | 19 |
| KKGLSKGCFGLKLDRIGSMSGLGCASLRDPRPNAPSTSA | 20 |

TABLE 2

| Exemplary natriuretic peptides | |
| --- | --- |
| Natriuretic peptides | SEQ ID NO: |
| ANKKGLSKGCFGLKLDRIGSMSGLGCPSLRDPRPNAPSTSA | 8 |
| ANKKGLGCFGLKLDRIGSMSGLGCPSLRDPRPNAPSTSA | 21 |
| ANKKGLSKGCFGLKLDRIGSMSGLGCSLRDPRPNAPSTSA | 22 |
| ANKKGLGCFGLKLDRIGSMSGLGCSLRDPRPNAPSTSA | 23 |
| ANKKGLRKGCFGLKLDRIGSMSGLGCPSLRDPRPNAPSTSA | 24 |
| ANKKGLDKGCFGLKLDRIGSMSGLGCPSLRDPRPNAPSTSA | 25 |
| ANKKGLSDGCFGLKLDRIGSMSGLGCPSLRDPRPNAPSTSA | 26 |
| ANKKGLSGGCFGLKLDRIGSMSGLGCPSLRDPRPNAPSTSA | 27 |
| ANKKGLSKGCFGLKLDRIGSMSGLGCPSLRDPRPNAPSTSA | 28 |
| ANKKGLSKGCFGLKLDRIGSMSGLGCDSLRDPRPNAPSTSA | 29 |
| ANKKGLSKGCFGLKLDRIGSMSGLGCASLRDPRPNAPSTSA | 30 |

TABLE 3

| Exemplary natriuretic peptides | |
| --- | --- |
| Natriuretic peptides | SEQ ID NO: |
| KGANKKGLSKGCFGLKLDRIGSMSGLGCPSLRDPRPNAPSTSA | 9 |
| KGANKKGLGCFGLKLDRIGSMSGLGCPSLRDPRPNAPSTSA | 31 |
| KGANKKGLSKGCFGLKLDRIGSMSGLGCSLRDPRPNAPSTSA | 32 |
| KGANKKGLGCFGLKLDRIGSMSGLGCSLRDPRPNAPSTSA | 33 |
| KGANKKGLRKGCFGLKLDRIGSMSGLGCPSLRDPRPNAPSTSA | 34 |
| KGANKKGLDKGCFGLKLDRIGSMSGLGCPSLRDPRPNAPSTSA | 35 |
| KGANKKGLSDGCFGLKLDRIGSMSGLGCPSLRDPRPNAPSTSA | 36 |
| KGANKKGLSGGCFGLKLDRIGSMSGLGCPSLRDPRPNAPSTSA | 37 |
| KGANKKGLSKGCFGLKLDRIGSMSGLGCPSLRDPRPNAPSTSA | 38 |
| KGANKKGLSKGCFGLKLDRIGSMSGLGCDSLRDPRPNAPSTSA | 39 |
| KGANKKGLSKGCFGLKLDRIGSMSGLGCASLRDPRPNAPSTSA | 40 |

TABLE 4

| Exemplary natriuretic peptides | |
| --- | --- |
| Natriuretic peptides | SEQ ID NO: |
| KYKGANKKGLSKGCFGLKLDRIGSMSGLGCPSLRDPRPNAPSTSA | 10 |
| ARKYKGANKKGLSKGCFGLKLDRIGSMSGLGCPSLRDPRPNAPSTSA | 41 |
| PNARKYKGANKKGLSKGCFGLKLDRIGSMSGLGCPSLRDPRPNAPSTSA | 42 |

TABLE 4-continued

| Exemplary natriuretic peptides | |
| --- | --- |
| Natriuretic peptides | SEQ ID NO: |
| EHPNARKYKGANKKGLSKGCFGLKLDRIGSMSGLGCPSLRDPRPNAPSTSA | 43 |
| LQEHPNARKYKGANKKGLSKGCFGLKLDRIGSMSGLGCPSLRDPRPNAPSTSA | 44 |
| RLLQEHPNARKYKGANKKGLSKGCFGLKLDRIGSMSGLGCPSLRDPRPNAPSTSA | 45 |
| WARLLQEHPNARKYKGANKKGLSKGCFGLKLDRIGSMSGLGCPSLRDPRPNAPSTSA | 46 |
| AAWARLLQEHPNARKYKGANKKGLSKGCFGLKLDRIGSMSGLGCPSLRDPRPNAPSTSA | 47 |
| SRAAWARLLQEHPNARKYKGANKKGLSKGCFGLKLDRIGSMSGLGCPSLRDPRPNAPSTSA | 48 |
| TKSRAAWARLLQEHPNARKYKGANKKGLSKGCFGLKLDRIGSMSGLGCPSLRDPRPNAPSTSA | 49 |
| VDTKSRAAWARLLQEHPNARKYKGANKKGLSKGCFGLKLDRIGSMSGLGCPSLRDPRPNAPSTS | 50 |

In some cases, an amino acid substitution can be a conservative amino acid substitution. For example, an amino acid residue of SEQ ID NO:7, 8, 9, or 10 can be selected and replaced with an amino acid residue that does not differ significantly in its effect on maintaining (a) the structure of the peptide backbone in the area of the substitution, (b) the charge or hydrophobicity of the molecule at the target site, or (c) the bulk of the side chain. For example, naturally occurring residues can be divided into groups based on side-chain properties: (1) hydrophobic amino acids (norleucine, methionine, alanine, valine, leucine, and isoleucine); (2) neutral hydrophilic amino acids (cysteine, serine, and threonine); (3) acidic amino acids (aspartic acid and glutamic acid); (4) basic amino acids (asparagine, glutamine, histidine, lysine, and arginine); (5) amino acids that influence chain orientation (glycine and proline); and (6) aromatic amino acids (tryptophan, tyrosine, and phenylalanine). Substitutions made within these groups can be considered conservative substitutions. Non-limiting examples of conservative substitutions include, without limitation, substitution of valine for alanine, lysine for arginine, glutamine for asparagine, glutamic acid for aspartic acid, serine for cysteine, asparagine for glutamine, aspartic acid for glutamic acid, proline for glycine, arginine for histidine, leucine for isoleucine, isoleucine for leucine, arginine for lysine, leucine for methionine, leucine for phenyalanine, glycine for proline, threonine for serine, serine for threonine, tyrosine for tryptophan, phenylalanine for tyrosine, and/or leucine for valine. Further examples of conservative substitutions that can be made within SEQ ID NO:7, 8, 9, or 10 are set forth in Table 5.

TABLE 5

| Examples of conservative amino acid substitutions | | |
| --- | --- | --- |
| Original Residue | Exemplary substitutions | Preferred substitutions |
| Ala | Val, Leu, Ile | Val |
| Arg | Lys, Gln, Asn | Lys |

TABLE 5-continued

Examples of conservative amino acid substitutions

| Original Residue | Exemplary substitutions | Preferred substitutions |
| --- | --- | --- |
| Asn | Gln, His, Lys, Arg | Gln |
| Asp | Glu | Glu |
| Cys | Ser | Ser |
| Gln | Asn | Asn |
| Glu | Asp | Asp |
| Gly | Pro | Pro |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, Gln, Asn | Arg |
| Met | Leu, Phe, Ile | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Norleucine | Leu |

In some cases, an amino acid substitution can be a non-conservative amino acid substitution. For example, an amino acid residue of SEQ ID NO:7, 8, 9, or 10 can be selected and replaced with an amino acid residue from a different class of amino acids as compared with the selected amino acid. For example, an acidic amino acid (aspartic acid or glutamic acid) present in SEQ ID NO:7, 8, 9, or 10 can be selected and replaced with a basic amino acid (asparagine, glutamine, histidine, lysine, or arginine).

A polypeptide described herein (e.g., a polypeptide having the amino acid sequence set forth in SEQ ID NO:7, 8, 9, or 10) can be obtained using any appropriate technique including, without limitation, solid phase polypeptide synthesis techniques such as those involving the use of an Applied BioSystems (Foster City, CA) Peptide Synthesizer or a Biosearch Inc. (San Rafael, CA) automatic peptide synthesizer. Disulfide bonds between cysteine residues can be introduced by mild oxidation of the linear polypeptides using KCN as described elsewhere (see, e.g., U.S. Pat. No. 4,757,048). In some cases, a polypeptide described herein (e.g., a polypeptide having the amino acid sequence set forth in SEQ ID NO:7, 8, 9, or 10) can be obtained recombinantly. For example, a polypeptide described herein (e.g., a polypeptide having the amino acid sequence set forth in SEQ ID NO:7, 8, 9, or 10) can be obtained by expressing a recombinant nucleic acid encoding the polypeptide such as an expression vector encoding a polypeptide described herein within host cells. The resulting polypeptide then can be purified using, for example, affinity chromatographic techniques and HPLC. The extent of purification can be measured using any appropriate method including, without limitation, column chromatography, polyacrylamide gel electrophoresis, or high-performance liquid chromatography. In some cases, a polypeptide described herein (e.g., a polypeptide having the amino acid sequence set forth in SEQ ID NO:7, 8, 9, or 10) can be designed or engineered to contain a tag sequence that allows the polypeptide to be purified (e.g., captured onto an affinity matrix) and/or an enzyme or label sequence that allows the polypeptide to be detected. For example, a tag such as c-myc, hemagglutinin, polyhistidine, or FLAG™ tag (Kodak) can be used to aid polypeptide purification. Examples of enzyme and label sequences that can be used to aid polypeptide detection include, without limitation, alkaline phosphatase, GFP, RFP, luciferases, and Cas polypeptides. Such tags, enzymes, and labels can be inserted anywhere within the polypeptide, including at either the carboxyl terminus or the amino terminus.

Any appropriate method can be used to confirm that a polypeptide described herein (e.g., a polypeptide having the amino acid sequence set forth in SEQ ID NO:7, 8, 9, or 10 with the exception that it includes one or more amino acid additions, deletions, or substitutions) has one or more natriuretic activities. For example, a polypeptide described herein can be confirmed as having a biological (e.g., natriuretic) activity in vitro by measuring its effect on cGMP levels generated by renal tubular cells and renal glomeruli or by testing its ability to suppress renal tubular apoptosis. A polypeptide described herein can be confirmed as having a biological (e.g., natriuretic) activity in vivo by, for example, testing its effects on factors such as pulmonary capillary wedge pressure, right atrial pressure, mean arterial pressure, urinary sodium excretion, urine flow, proximal and distal fractional sodium reabsorption, plasma renin activity, plasma and urinary cGMP levels, glomerular filtration rate, and/or left ventricular mass in animals after induced myocardial infarction using methods such as those described elsewhere (e.g., WO 2009/149161).

In some cases, a polypeptide described herein (e.g., a polypeptide having the amino acid sequence set forth in SEQ ID NO:7, 8, 9, or 10) can be formulated as a pharmaceutical composition by admixture with one or more pharmaceutically acceptable non-toxic excipients or carriers. Pharmaceutical compositions can be prepared for parenteral administration, for example, in the form of liquid solutions or suspensions in aqueous physiological buffer solutions; for oral administration, for example, in the form of tablets or capsules; or for intranasal administration, for example in the form of powders, nasal drops, or aerosols. Compositions for other routes of administration can be prepared as desired using appropriate methods.

Formulations for parenteral administration can include as common excipients, sterile water, saline, polyalkylene glycols such as polyethylene glycol, oils of vegetable origin, hydrogenated naphthalenes, and combinations thereof. In some cases, biocompatible, biodegradable lactide polymer, lactide/glycolide copolymer, polyoxethylene-polyoxypropylene copolymers, or combinations thereof can be used as excipients for controlling the release of the polypeptide in vivo. Other suitable parenteral delivery systems that can be used include, without limitation, ethylene-vinyl acetate copolymer particles, osmotic pumps, implantable infusion systems, liposomes, and combinations thereof. Formulations for inhalation administration can include excipients such as lactose. Inhalation formulations can be aqueous solutions containing, for example, polyoxyethylene-9-lauryl ether, glycocholate, deoxycholate, or combinations thereof, or they can be oily solutions for administration in the form of nasal drops. If desired, a composition containing a polypeptide described herein (e.g., a polypeptide having the amino acid sequence set forth in SEQ ID NO:7, 8, 9, or 10) can be formulated as a gel to be applied intranasally. Formulations for parenteral administration can include glycocholate for buccal administration.

For oral administration, tablets or capsules can be prepared using appropriate methods with pharmaceutically acceptable excipients such as binding agents (e.g., pregelatinized maize starch, polyvinylpyrrolidone, or hydroxypropyl methylcellulose); fillers (e.g., lactose, microcrystalline cellulose or calcium hydrogen phosphate); lubricants (e.g. magnesium stearate, talc or silica); disintegrants (e.g., potato starch or sodium starch glycolate); or wetting agents (e.g., sodium lauryl sulfate). Tablets can be coated using appropriate methods. Preparations for oral administration can be formulated to give controlled release of the polypeptide.

Nasal preparations can be presented in a liquid form or as a dry product. Nebulised aqueous suspensions or solutions can include carriers or excipients to adjust pH and/or tonicity.

This document also provides methods and materials for treating a mammal that has ADHF, is developing ADHF, is likely to develop more severe effects of ADHF, and/or is likely to experience a poor outcome from ADHF (e.g., rehospitalization or rehospitalization and death). For example, a mammal can be assessed to determine if the mammal has an elevated plasma CNP level and an elevated urinary CNP level. As described herein, mammals having an elevated level of plasma CNP and an elevated level of urinary CNP can be developing or can be likely to develop more severe effects of ADHF, or can be likely to experience a poor outcome from ADHF. In some cases, once a mammal is identified as having an elevated level of plasma CNP and an elevated level of urinary CNP, that mammal can be monitored for the presence of a more severe effect of ADHF. For example, the mammal can be monitored or evaluated for the presence of more severe cardiac dysfunction, reduced estimated glomerular filtration rate (eGFR), and/or atrial fibrillation. Once a mammal having an elevated level of plasma CNP and an elevated level of urinary CNP is identified, that mammal can be treated with one or more natriuretic peptides to reduce a symptom of ADHF, to counter-act a symptom of ADHF, and/or to reduce the likelihood of a poor outcome from ADHF. Examples of natriuretic peptides that can be used alone or in combination to treat a mammal as described herein include, without limitation, CD-NP, a CD-NP variant having the amino acid sequence set forth in SEQ ID NO:1 with one to ten (e.g., one, two, three, four, five, six, seven, eight, nine, or ten) amino acid additions, deletions, or substitutions provided that the two cysteine residues are maintained and are the only two cysteine residues of the natriuretic peptide, a natriuretic peptide having the amino acid sequence set forth in SEQ ID NO:7, a natriuretic peptide having the amino acid sequence set forth in SEQ ID NO:7 with one to ten (e.g., one, two, three, four, five, six, seven, eight, nine, or ten) amino acid additions, deletions, or substitutions provided that the two cysteine residues are maintained and are the only two cysteine residues of the natriuretic peptide, a natriuretic peptide having the amino acid sequence set forth in SEQ ID NO:8, a natriuretic peptide having the amino acid sequence set forth in SEQ ID NO:8 with one to ten (e.g., one, two, three, four, five, six, seven, eight, nine, or ten) amino acid additions, deletions, or substitutions provided that the two cysteine residues are maintained and are the only two cysteine residues of the natriuretic peptide, a natriuretic peptide having the amino acid sequence set forth in SEQ ID NO:9, a natriuretic peptide having the amino acid sequence set forth in SEQ ID NO:9 with one to ten (e.g., one, two, three, four, five, six, seven, eight, nine, or ten) amino acid additions, deletions, or substitutions provided that the two cysteine residues are maintained and are the only two cysteine residues of the natriuretic peptide, a natriuretic peptide having the amino acid sequence set forth in SEQ ID NO:10, a natriuretic peptide having the amino acid sequence set forth in SEQ ID NO:10 with one to ten (e.g., one, two, three, four, five, six, seven, eight, nine, or ten) amino acid additions, deletions, or substitutions provided that the two cysteine residues are maintained and are the only two cysteine residues of the natriuretic peptide, a natriuretic peptide that can activate GC-A, and a natriuretic peptide that can activate GC-B.

In some cases, one or more additional therapeutic agents also can be administered to a mammal (e.g., a mammal identified as having an elevated plasma CNP level and an elevated urinary CNP level) in addition to one or more natriuretic peptides, in order to reduce a symptom of ADHF, to counter-act a symptom of ADHF, and/or to reduce the likelihood of a poor outcome from ADHF. Examples of such therapeutic agents include, without limitation, ACE inhibitors (ACEi's), angiotensin II receptor blockers (ARBs; e.g., ARBs neprilysin inhibition such as sacubitril-valsartan), aldosterone antagonists, diuretics (e.g., furosemide, bumetanide, ethacrynic acid, torsemide, acetazolamide, dorzolamide, amiloride, spironolactone, eplerenone, triamterene, potassium canrenoate, bendroflumethiazide, or hydrochlorothiazide), beta-blockers, and statins. The one or more natriuretic peptides and the one or more additional therapeutic agents can be administered simultaneously (e.g., in the same composition or in separate compositions that are administered at the same time), or sequentially.

Any appropriate route of administration can be used to administer a composition containing one or more natriuretic peptides (or one or more natriuretic peptides in combination with one or more additional therapeutic agents) to treat a mammal that has ADHF, is developing ADHF, is likely to develop more severe effects of ADHF, and/or is likely to experience a poor outcome from ADHF. For example, parenteral administration (e.g., by subcutaneous, intrathecal, intraventricular, intramuscular, or intraperitoneal injection, or by intravenous drip) can be used to administer a composition containing one or more natriuretic peptides (or one or more natriuretic peptides in combination with one or more additional therapeutic agents) to a mammal (e.g., a human). In some cases, the administration can be rapid (e.g., by injection) or can occur over a period of time (e.g., by slow infusion or administration of slow release formulations). In some cases, a composition containing one or more natriuretic peptides (or one or more natriuretic peptides in combination with one or more additional therapeutic agents) can be administered to a mammal (e.g., a human) via topical administration (e.g., transdermal, sublingual, ophthalmic, or intranasal), pulmonary administration (e.g., by inhalation or insufflation of powders or aerosols), or oral administration.

In some cases, a mammal having an elevated plasma CNP level and an elevated urinary CNP level can be instructed to self-administer one or more natriuretic peptides (and, in some cases, one or more additional therapeutic agents) as described herein.

A composition containing one or more natriuretic peptides such as CD-NP or a natriuretic peptide having the amino acid sequence set forth in SEQ ID NO:7, 8, 9, or 10 (or one or more natriuretic peptides in combination with one or more additional therapeutic agents) can be administered to a mammal (e.g., a human) in an appropriate amount, at an appropriate frequency, and for an appropriate duration effective to achieve a desired outcome (e.g., reduced severity of a symptom of ADHF).

In some cases, a composition containing one or more natriuretic peptides such as CD-NP or a natriuretic peptide having the amino acid sequence set forth in SEQ ID NO:7, 8, 9, or 10 (or one or more natriuretic peptides in combination with one or more additional therapeutic agents) can be administered to a mammal identified as having an elevated level of plasma CNP and an elevated level of urinary CNP to reduce the severity of a symptom of ADHF by, for example, at least 5 percent (e.g., at least 10 percent, at least 25 percent, at least 50 percent, at least 75 percent, or 100 percent). Any appropriate method can be used to determine whether or not a mammal (e.g., a human) has experienced a reduction in the severity of a symptom of ADHF.

An effective amount of a composition containing one or more natriuretic peptides such as CD-NP or a natriuretic peptide having the amino acid sequence set forth in SEQ ID NO:7, 8, 9, or 10 (or one or more natriuretic peptides in combination with one or more additional therapeutic agents) can be any amount that reduces a symptom of ADHF without producing significant toxicity to the mammal. An effective amount can vary depending on the relative potency of the peptide, and can generally be estimated based on $EC_{50}$ found to be effective in in vitro and in vivo animal models. Typically, an effective amount of a natriuretic peptide described herein (e.g., CD-NP or a natriuretic peptide having the amino acid sequence set forth in SEQ ID NO:7, 8, 9, or 10) is from about 1 μg to about 100 μg per kg of body weight. For example, an effective amount of a natriuretic peptide such as CD-NP or a natriuretic peptide having the amino acid sequence set forth in SEQ ID NO:7, 8, 9, or 10 can be from 1 to 5 μg/kg, from 5 to 10 μg/kg, from 7 to 15 μg/kg, from 10 to 20 μg/kg, from 14 to 22 μg/kg, from 20 to 50 μg/kg, from 22 to 29 μg/kg, from 50 to 75 μg/kg, or from 75 to 100 μg/kg. If a particular mammal fails to respond to a particular amount, then the amount can be increased by, for example, two-fold. After receiving this higher amount, the subject can be monitored for both responsiveness to the treatment and toxicity symptoms, and adjustments made accordingly. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the condition (e.g., ADHF) may require an increase or decrease in the actual effective amount administered.

A composition containing one or more natriuretic peptides such as CD-NP or a natriuretic peptide having the amino acid sequence set forth in SEQ ID NO:7, 8, 9, or 10 (or one or more natriuretic peptides in combination with one or more additional therapeutic agents) can be administered once or more than once, at any appropriate frequency and for any appropriate duration. An effective frequency for administering a composition containing one or more natriuretic peptides such as CD-NP or a natriuretic peptide having the amino acid sequence set forth in SEQ ID NO:7, 8, 9, or 10 (or one or more natriuretic peptides in combination with one or more additional therapeutic agents) can be any frequency that reduces the severity of a symptom of ADHF without producing significant toxicity to the mammal. For example, the frequency of administration can be once or more daily, biweekly, weekly, monthly, or even less. The frequency of administration can remain constant or can be variable during the duration of treatment. In some cases, a course of treatment can include rest periods. For example, a composition containing one or more natriuretic peptides such as CD-NP or a natriuretic peptide having the amino acid sequence set forth in SEQ ID NO:7, 8, 9, or 10 (or one or more natriuretic peptides in combination with one or more additional therapeutic agents) can be administered over a two week period followed by a two week rest period, and then repeated. As with the effective amount, various factors can influence the actual frequency of administration. For example, the effective amount, duration of treatment, use of multiple treatment agents, route of administration, and severity of the condition (e.g., ADHF) symptoms may require an increase or decrease in administration frequency.

An effective duration for administering a composition containing one or more natriuretic peptides such as CD-NP or a natriuretic peptide having the amino acid sequence set forth in SEQ ID NO:7, 8, 9, or 10 (or one or more natriuretic peptides in combination with one or more additional therapeutic agents) can be any duration that reduces the severity of a symptom of ADHF without producing significant toxicity to the mammal. In some cases, the effective duration can vary from several hours to several days, or even weeks or months. In general, an effective duration for administering a composition containing one or more natriuretic peptides such as CD-NP or a natriuretic peptide having the amino acid sequence set forth in SEQ ID NO:7, 8, 9, or 10 (or one or more natriuretic peptides in combination with one or more additional therapeutic agents) can range from about 24 to about 96 hours (e.g., from 24 to 96 hours, from 24 to 48 hours, from 48 to 72 hours, or from 72 to 96 hours). In some cases, an effective duration can be for as long as the individual mammal (e.g., a human) is alive. Multiple factors can influence the actual effective duration used for a particular treatment. For example, an effective duration can vary with the frequency of administration, effective amount, use of multiple treatment agents, route of administration, and severity of the condition (e.g., ADHF).

In some cases, a composition containing one or more natriuretic peptides such as CD-NP or a natriuretic peptide having the amino acid sequence set forth in SEQ ID NO:7, 8, 9, or 10 can be administered at a dose of about 0.001 to about 0.010 μg/kg/min for 24 to 96 hours (e.g., about 0.005 μg/kg/min for 48 to 72 hours).

After administering a composition containing one or more natriuretic peptides such as CD-NP or a natriuretic peptide having the amino acid sequence set forth in SEQ ID NO:7, 8, 9, or 10 to a mammal (e.g., a human), the mammal can be monitored to determine whether or not the treatment was effective against ADHF. For example, a mammal (e.g., a human) can be assessed after treatment to determine whether or not cardiac and/or renal function was reduced. Any appropriate method can be used to assess cardiac and/or renal function. For example, plasma NT-proBNP (N-terminal pro-B type natriuretic peptide), serum cr, eGFR, shortness of breath, edema, and/or lung congestion can be used to monitor an effective response to a treatment described herein.

The invention will be further described in the following examples, which do not limit the scope of the invention described in the claims.

EXAMPLES

Example 1—Materials and Methods

Study populations: Healthy subjects and ADHF patients were prospectively recruited. Healthy subjects were non-smokers, had no history of cardiovascular (CV) or systemic disease, and were not taking any CV medications. Hospitalized ADHF patients were identified and enrolled from an ongoing registry of consecutive admissions between 2009 and 2016, and only those with a clinical diagnosis of HF consistent with the Framingham criteria (Mahmood and Wang *Glob Heart* 8(1):77-82, 2013) were included. Baseline history assessment, physical examination, and transthoracic echocardiography were conducted as part of routine clinical care. A total of 109 healthy subjects and 208 ADHF patients had both plasma and urine samples available for CNP measurement and were included in the study.

Plasma and urine samples: Plasma and urine sample were collected from healthy subjects upon enrollment. For ADHF patients, plasma and 24-hour urine samples were obtained within 72 hours of admission. All urine samples were collected with 50% acetic acid (30 mL of 1:1 acetic acid; 17.4M) as preservative on ice. The total volume for each sample was recorded and samples were aliquoted and stored at −80° C. Plasma creatinine and NT-proBNP were measured using standard procedures in a clinical chemistry laboratory, and urinary creatinine and protein were measured using standard procedures in a renal testing laboratory. All urinary components were normalized to urinary creatinine to reduce variation associated with volume difference. The plasma creatinine levels were 0.83 [interquartile range (IQR): 0.75-0.96] mg/dL in healthy subjects and 1.3 (IQR: 1.0-1.6) mg/dL in ADHF patients. The urinary creatinine levels were 70 (IQR: 32-130) mg/dL in healthy subjects and 43 (IQR: 28-75) mg/dL in ADHF patients. Estimated glomerular filtration rate (eGFR) was calculated using the chronic kidney disease epidemiology collaboration (CKD-EPI) equation.

Plasma and urinary CNP: Plasma and urinary CNP were measured using a commercially available non-equilibrium radioimmunoassay kit from Phoenix Pharmaceutical (Burlingame, CA), using an antibody against human CNP-22 as reported elsewhere (Sangaralingham et al., *Am J Physiol Renal Physiol.* 2011, 301(5):F943-952) with modifications. For CNP quantification, 100 µl of plasma or urine were incubated with 100 µl of CNP antibody at 4° C. for 18 hours. 100 µl (10,000 counts) of $^{125}$I-labeled CNP was added and incubated at 4° C. for another 18 hours. Normal rabbit serum and goat anti-rabbit serum were then added to all samples to separate the free and bound fractions, and samples were centrifuged, the free fraction was aspirated, and the bound fraction was counted on a gamma counter. The range of the standard curve used in the assay was 0.5 to 128 pg, with the lowest detection of 0.5 pg. Inter- and intra-assay variability were 13% and 6%, respectively. Cross-reactivity was <1% with ANP and BNP. The fractional CNP excretion was calculated with the formula: (urinary CNP×plasma creatinine)/(plasma CNP×urinary creatinine).

Statistical analysis: Descriptive variables were presented as mean±SD for those following a normal distribution and as median (interquartile range [IQR]) for those in all tables that did not follow an approximate normal distribution. Comparisons between healthy subjects and ADHF patients were conducted using appropriate linear or logistic regression methods to allow adjustment for age, sex, and BMI. Urinary CNP, plasma CNP and plasma NT-proBNP were right-skewed distributed in both healthy subjects and ADHF patients, and thus were log-transformed to normalize the distributions. Pearson's correlation coefficients were used to determine the correlation between urinary CNP and plasma CNP after log transformation. Multivariable regression models were constructed to determine independent characteristics associated with the log transformed plasma CNP and urinary CNP levels, incorporating variables with univariable association significant at P<0.10.

Urinary and plasma CNP concentrations in healthy subjects were referred to set thresholds for the stratification of ADHF patients as reported elsewhere (Reginauld et al., *JACC Heart Fail.* 2019, 7(10):891-898). Specifically, patients were classified as having normal CNP levels if their urinary or plasma levels were below the 95th percentile of the healthy subjects, or were classified as having elevated CNP levels if their levels were greater than or equal to the 95th percentile threshold. All-cause rehospitalization and all-cause mortality were ascertained from institutional records, including local primary care data. Patients were otherwise censored at the time of last known clinical follow-up. Event free survival curves were generated using the Kaplan-Meier method based on time to event outcomes and comparisons between groups were performed with log-rank test. Cox proportional hazards regression methods were used to study the association between time to event outcomes and CNP levels while accounting for other important covariates. Results of these analyses were presented with hazard ratio (HR) and corresponding 95% confidence limit. C-statistic and integrated discrimination index (IDI) were calculated to quantify discriminatory ability and to evaluate the improvement in prediction accuracy of the combination of urinary and plasma CNP over base model and plasma NT-proBNP, for outcomes. IDI confidence intervals and comparison P-values were derived based on 1000 bootstrap samples. SAS version 9.4 and JMP (Cary, NC) were used for analyses and two-sided P<0.05 was considered statistically significant.

Example 2—Results

Study Populations: Baseline clinical characteristics are shown in Table 6. Compared to healthy subjects, ADHF patients were older, mostly male, and had higher BMI and lower estimated glomerular filtration rate (eGFR) (P<0.001 for all). ADHF patients had a number of comorbidities and were taking a number of CV medications, and the median length of hospital stay (LOHS) was 6 (IQR: 4-10) days. 45% of patients were New York Heart Association (NYHA) class 3 and had a mean LVEF of 37±17%. The level of plasma NT-proBNP was significantly elevated in ADHF patients [2796 (IQR: 1286-7029) pg/mL] compared to healthy subjects [56 (IQR: 29-85) pg/mL]. The urinary protein levels between healthy subjects [0.07 (IQR: 0.05-0.09) mg/mg Cr] and ADHF patients [0.05 (IQR: 0.03-0.12) mg/mg Cr] were not significantly different (P=0.10).

Figure 1B:
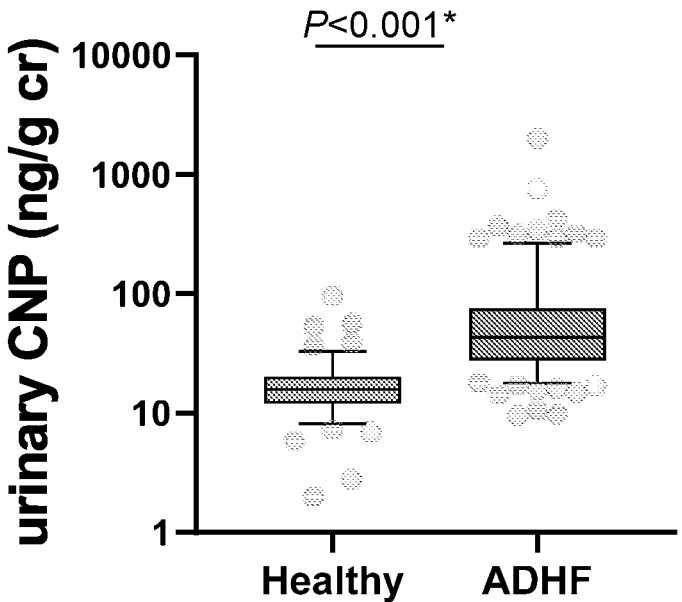
FIG. 1B is a graph plotting urinary CNP levels in healthy subjects and ADHF patients. The P values shown FIGS. 1A and 1B were adjusted for age, sex, and body mass index (BMI).
Figure 1C:
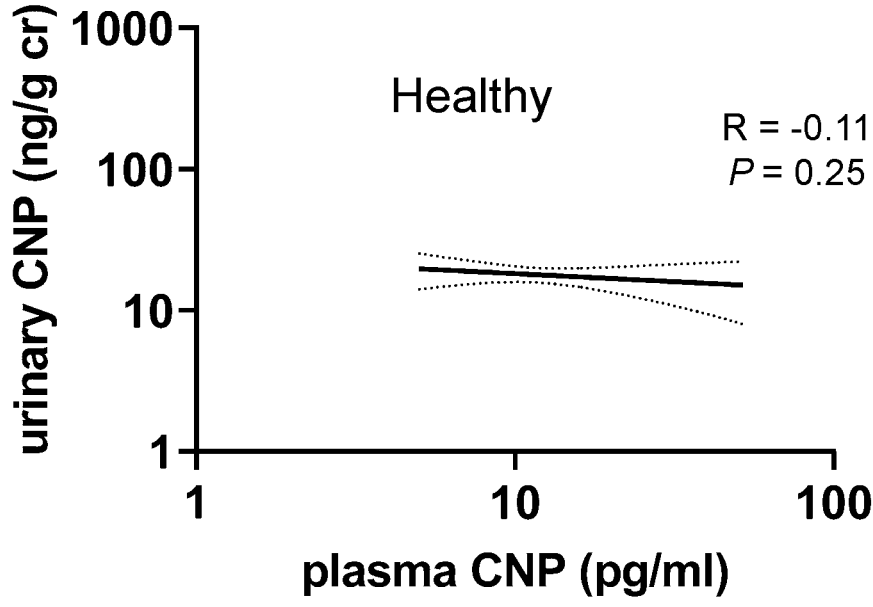
FIG. 1C is a graph plotting the correlation between urinary and plasma CNP in healthy subjects.
Figure 1D:
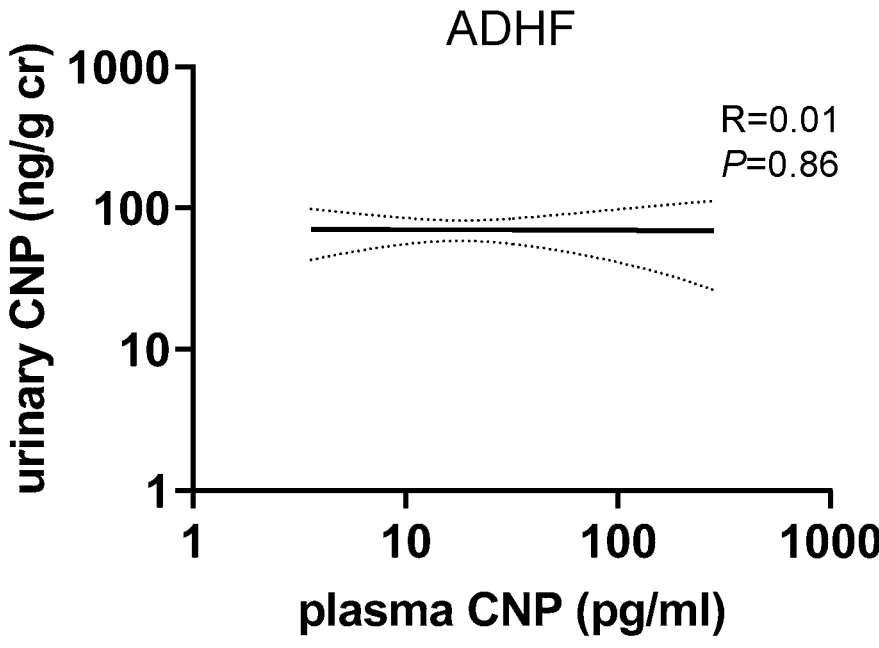
FIG. 1D is a graph plotting the correlation between urinary and plasma CNP in ADHF patients.

Plasma and urinary CNP levels: In healthy subjects, plasma CNP was 11.8 (IQR: 9.5-15.0) pg/mL and urinary CNP was 15.8 (IQR: 12.1-20.2) ng/g cr. In ADHF patients, both plasma CNP [18.2 (IQR: 10.7-30.3) pg/mL] and urinary CNP [43.1 (IQR: 27.9-74.7) ng/g Cr] were significantly elevated as compared to healthy subjects (Table 6 and FIGS. 1A and 1B, P<0.001 for both after adjusting for age, sex, and BMI). Importantly, no correlation was found between plasma and urinary CNP in healthy subjects or in ADHF patients (FIGS. 1C and 1D), indicating that urinary CNP reflects renal-derived CNP and thus is independent of circulating CNP. The accuracy of urinary and plasma CNP in diagnosing ADHF was evaluated by area under the curve (AUC) and positive predictive value (PPV). For patients with ADHF, the AUC for elevated urinary CNP was 0.92 (95% CI: 0.89-0.95) with a PPV of 93.1% (95% CI: 88.5-96.3%), while the AUC for elevated plasma CNP was 0.69 (95% CI: 0.64-0.75) with a PPV of 92.6% (95% CI: 86.0-96.8%). Further, the fractional CNP excretion in ADHF patients [0.04 (IQR: 0.02-0.07)] was 4 times higher than in healthy subjects [0.01 (IQR: 0.01-0.02)].

Figure 2A:
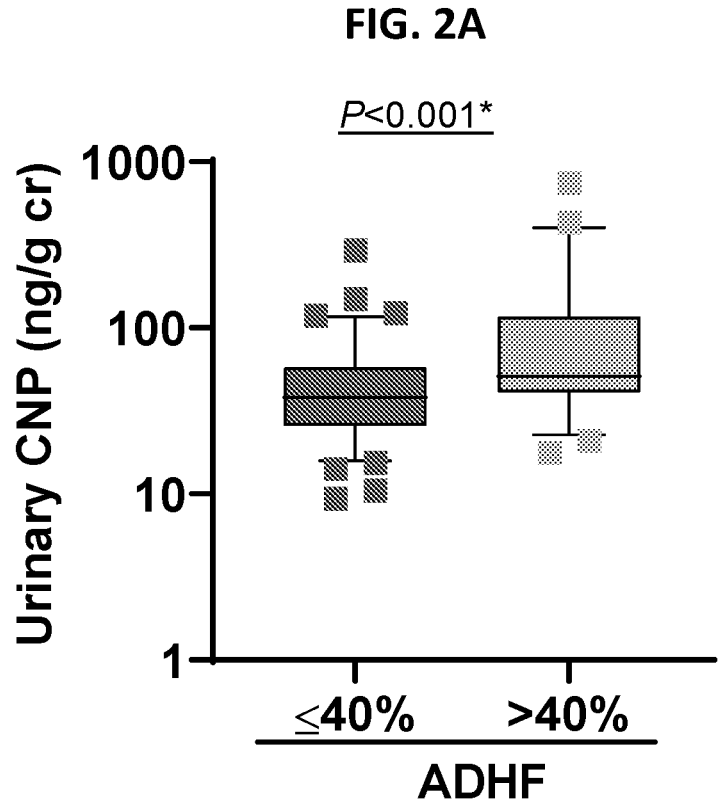
FIGS. 2A-2C are graphs plotting levels of urinary CNP (FIG. 2A), plasma N-terminal pro-B type natriuretic peptide (NT-proBNP.
Figure 2B:
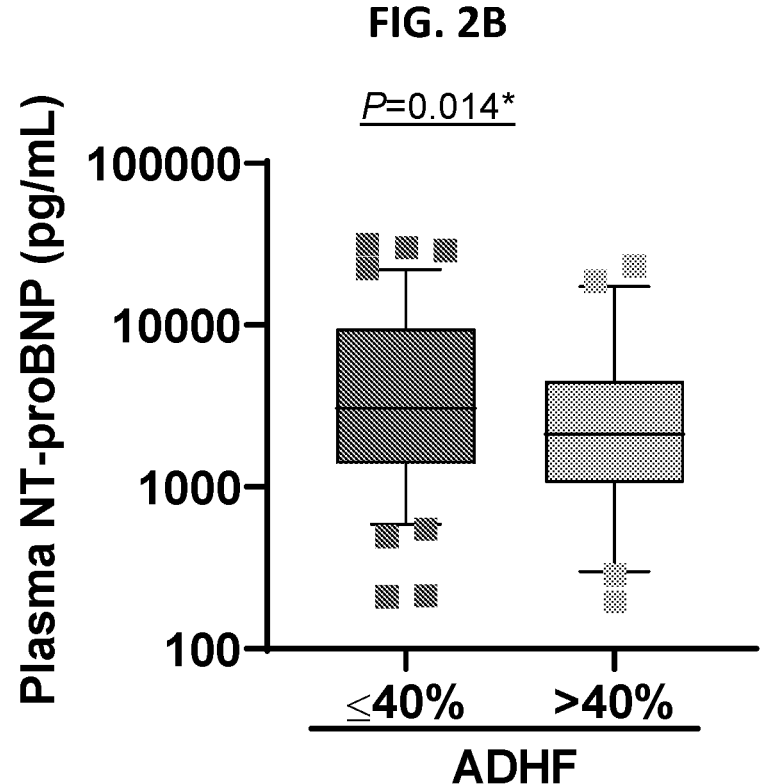
Figure 2C:
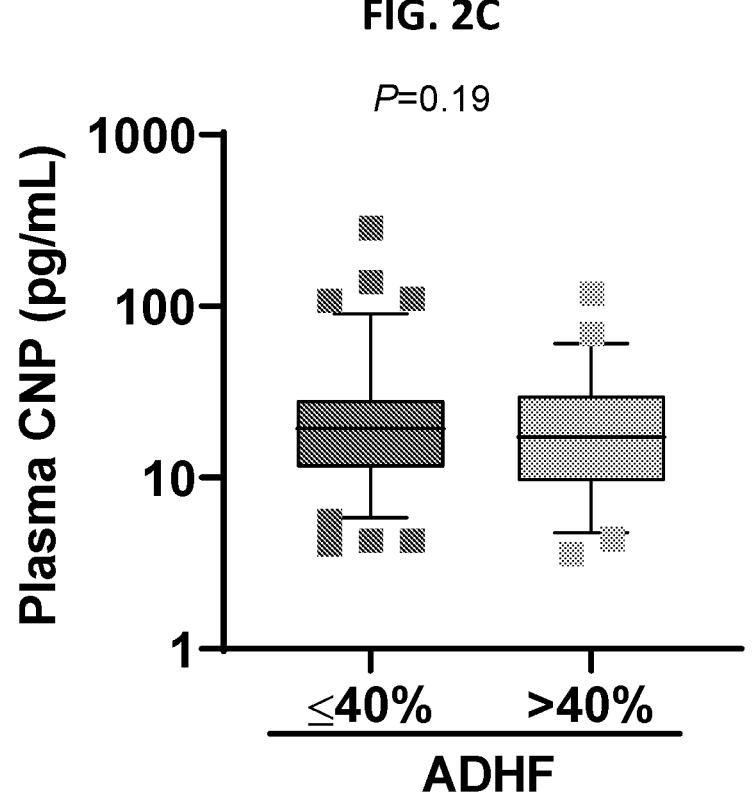

Clinical associates of CNP in healthy subjects and ADHF patients: Univariable and multivariable regression analysis were conducted in healthy (Tables 7A and 7B) and ADHF (Tables 8A and 8B) cohorts. In healthy subjects, neither urinary nor plasma CNP were associated with age, sex, or BMI. In contrast, plasma NT-proBNP was affected by age and sex even after multivariable adjustment. In addition, urinary CNP was positively associated with eGFR, while plasma NT-proBNP was negatively associated with eGFR. In ADHF patients, multivariable analysis revealed that plasma CNP was positively correlated with LOHS, while urinary CNP was positively correlated with female sex and LVEF. When ADHF patients were separated by LVEF ≤40% (reduced EF) and LVEF >40% (preserved EF), ADHF patients with preserved EF had significantly higher urinary CNP (FIG. 2A) and lower plasma NT-proBNP (FIG. 2B) compared to ADHF patients with reduced EF, while no differences were observed for plasma CNP (FIG. 2C). Moreover, there was no significant association of CV medication or comorbidities with urinary and plasma CNP levels. Notably, despite the significant positive correlation of urinary and plasma CNP with plasma NT-proBNP, the clinical associations of urinary and plasma CNP were markedly different from those of plasma NT-proBNP in ADHF patients.

Contemporary normal values of plasma and urinary CNP defined with healthy subjects: As shown in Table 9, the 95th percentile of plasma CNP (24.7 pg/mL) and urinary CNP (33.1 ng/g Cr) in healthy subjects was defined as the highest normal level under the physiological condition. These cutoff values were leveraged as cutoffs to determine a normal or elevated status of plasma and urinary CNP in ADHF patients.

Figure 3:
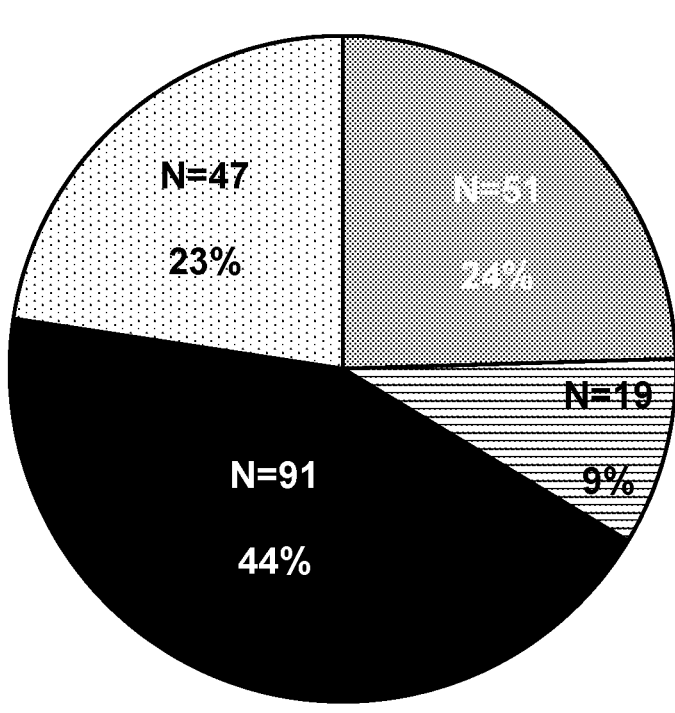
FIG. 3 is a pie chart indicating subgroup characterization of ADHF patients based on elevated or normal CNP levels in the plasma and urine.

Characterization of ADHF patients with normal and elevated plasma and urinary CNP levels: As illustrated in FIG. 3, 23% of ADHF patients had elevated plasma and urinary CNP, 44% had normal plasma CNP and elevated urinary CNP, 9% had elevated plasma CNP and normal urinary CNP, and 24% had normal plasma and urinary CNP. Demographic and clinical characteristics among the 4 subgroups and shown in Table 10. The LVEF, eGFR, LOHS, the presence of atrial fibrillation (AF) and plasma NT-proBNP levels were found to be different among subgroups (P<0.05 for all), after adjusting for age and sex.

The subgroup with elevated levels of both plasma and urinary CNP was associated with more severe cardiac dysfunction, as evidenced by the highest level of plasma NT-proBNP [7441 (IQR: 3462, 14029) pg/mL]. This cohort also had the lowest eGFR (49±21 mL/min/1.73 m²), the longest LOHS [7 (4, 17) days], and the highest proportion of atrial fibrillation (74%). The subgroup with elevated urinary CNP and normal plasma CNP had the highest LVEF (42±18%). In contrast, the subgroup with elevated plasma CNP and normal urinary CNP was similar in regard to clinical characteristics to the subgroup with normal levels of both plasma and urinary CNP (P>0.05 for all, multiple comparisons).

Clinical outcomes: During a median (IQR) follow-up of 3.0 (1.0, 4.9) years, the composite clinical outcome (all-cause rehospitalization and deaths) occurred in 176 ADHF patients. There were 114 deaths and 131 hospitalizations. The rates of events at 3 years were 42% for death, 70% for rehospitalization, and 77% for rehospitalization/death.

Figure 4A:
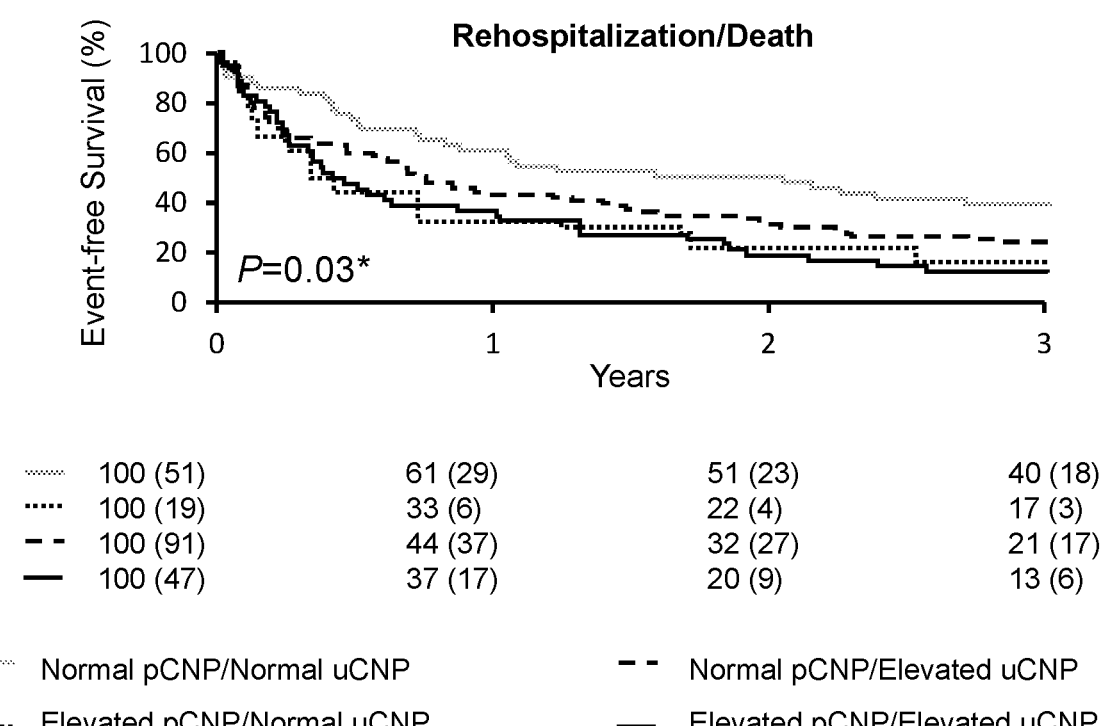
FIGS. 4A-4C are graphs plotting clinical outcomes in ADHF patients with regard to rehospitalization/death (FIG. 4A), rehospitalization (FIG. 4B), and death (FIG. 4C).
Figure 4B:
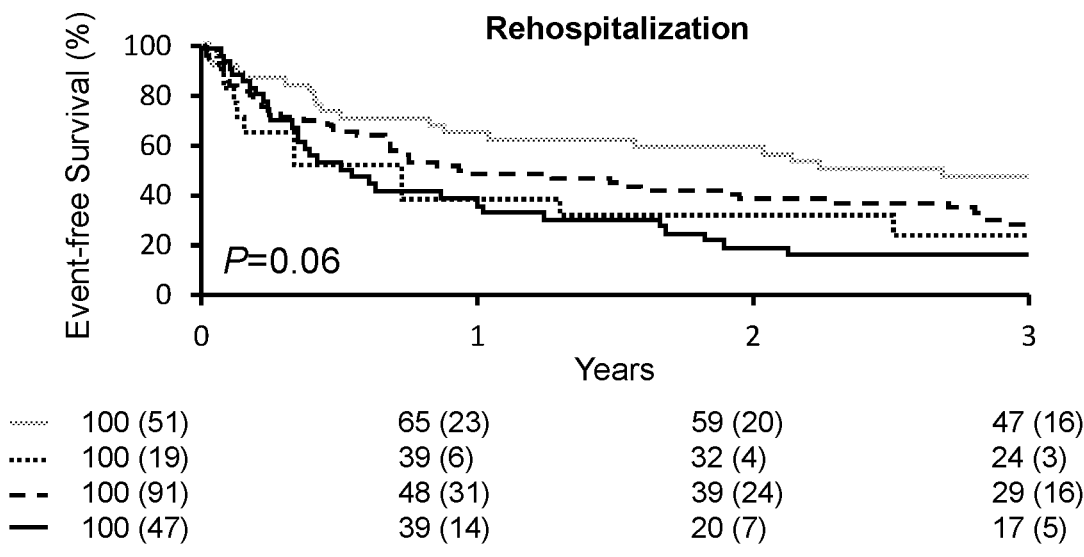
Figure 4C:
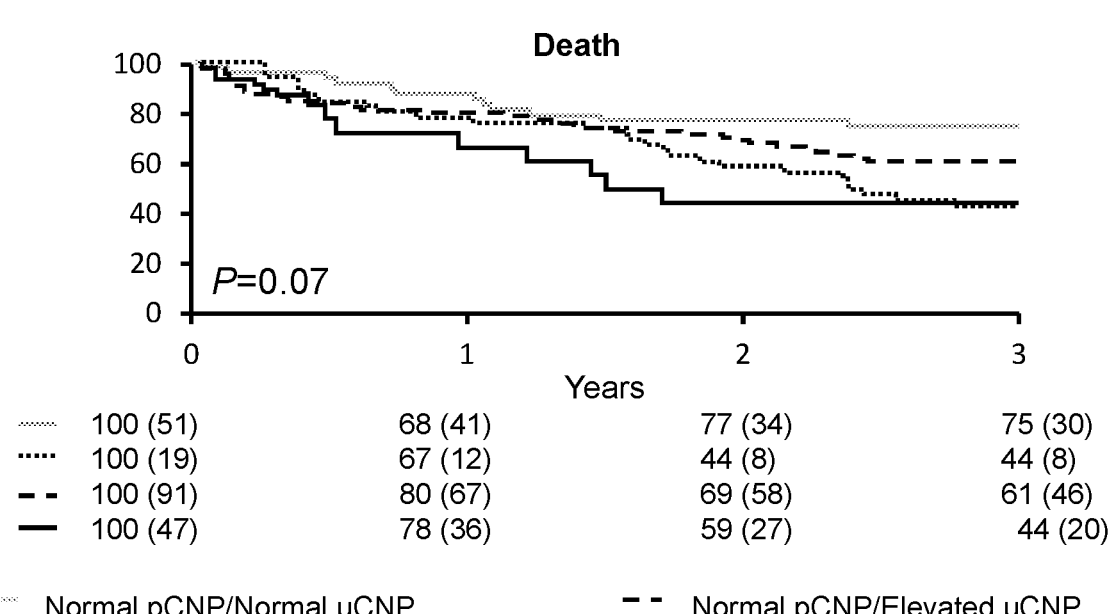

As illustrated in FIGS. 4A-4C, Kaplan Meier curves revealed persistent divergence of event-free survival rates out to 3 years, particularly in ADHF patients with both elevated plasma and urinary CNP. Given this observation, multivariate Cox models were constructed to examine the combination of plasma and urinary CNP both being normal, one (either plasma or urinary CNP) being elevated, or both plasma and urinary CNP being elevated, in order to examine the incremental risk predicted by these combinations (Table 11). Compared with the risk when both plasma and urinary CNP were normal (the reference group), only the group with an elevation in both plasma and urinary CNP showed a significantly higher risk of rehospitalization/death [HR: 1.79 (95% CI: 1.07-3.02), P=0.03] and rehospitalization [HR: 2.16 (95% CI: 1.16-4.03), P=0.01], even after adjusting for age, sex, eGFR, urinary protein/creatinine ratio, LVEF, and plasma NT-proBNP. The risk of death alone was not different significantly among four subgroups in all adjusted models.

The added predictive value of urinary and plasma CNP on rehospitalization/death and rehospitalization were further assessed by calculating the c-statistic and IDI (Table 12). Compared to a base model of risk factors, with and without plasma NT-proBNP included, the addition of urinary and plasma CNP together showed a moderate increase in c-statistic for both outcomes. Significant increases in the IDI and relative IDI (ranging from 30-49%), further supported the added value of urinary and plasma CNP to established clinical risk factors in predicting the risk of rehospitalization/death and rehospitalization in ADHF patients.

TABLE 6

| Clinical Characteristics | | | |
|---|---|---|---|
| Characteristic | Healthy Subjects (n = 109) | ADHF Patients (n = 208) | Adjusted P Value |
| Age, years | 56 ± 12 | 69 ± 13 | <0.001 |
| Sex, female (%) | 70 | 32 | <0.001 |
| BMI, kg/m² | 27 ± 5 | 32 ± 8* | <0.001 |
| LVEF (%) | — | 37 ± 19† | |
| eGFR (mL/ min/1.73 m²) | 85 ± 13 | 58 ± 24 | <0.001 |
| Length of hospital stay (days) | — | 6 (4, 10) | |
| Comorbidities | | | |
| Hypertension, n (%) | — | 150 (72%) | |
| Diabetes, n (%) | — | 79 (38%) | |
| Atrial fibrillation, n (%) | — | 125 (60%) | |
| Ischemic heart disease, n (%) | — | 130 (63%) | |
| Myocardial infarction, n (%) | — | 47 (23%) | |
| Hyperlipidemia, n (%) | — | 136 (66%) | |
| Stroke, n (%) | — | 10 (5%) | |
| Medications | | | |
| ACEi or ARB, n (%) | — | 134 (64%) | |
| Beta-blocker, n (%) | — | 135 (65%) | |
| Loop diuretic, n (%) | — | 203 (97%) | |
| Statin, n (%) | — | 124 (59%) | |
| Plasma Variables | | | |
| NT-proBNP, pg/mL | 56 (29, 85) | 2791 (1286, 7029) | <0.001 |
| CNP, pg/mL | 11.8 (9.5, 15.0) | 18.2 (10.7, 30.3) | <0.001 |
| Urinary Variables | | | |
| Creatinine (Cr), mg/dl | 70 (32, 130) | 43 (28, 75) | <0.001 |
| CNP, ng/g Cr | 15.8 (21.1, 20.2) | 43.1 (27.9, 74.7) | <0.001 |

Values are presented as mean ± SD, n (%), or median (interquartile range).
*n = 154;
†n = 198.
P values have been adjusted for age, sex, and BMI.

TABLE 7A

Univariable Analysis of Urinary CNP, Plasma CNP, and Plasma NT-proBNP in Healthy Subjects

| Predictors (Univariable) | $Log_{10}$(urinary CNP) β (SE) | r | P Value | $Log_{10}$(plasma CNP) β (SE) | r | P Value | $Log_{10}$(plasma NT-proBNP) β (SE) | r | P Value |
|---|---|---|---|---|---|---|---|---|---|
| Age | 0.002 (0.002) | 0.13 | 0.19 | −0.001 (0.001) | −0.08 | 0.41 | 0.02 (0.002) | 0.54 | <0.001 |
| Sex, female | 0.05 (0.02) | 0.22 | 0.02 | −0.03 (0.02) | −0.18 | 0.06 | 0.11 (0.04) | 0.29 | 0.002 |
| BMI | −0.003 (0.005) | −0.07 | 0.49 | 0.005 (0.004) | 0.14 | 0.14 | −0.006 (0.008) | 0.08 | 0.43 |
| eGFR | 0.003 (0.002) | 0.17 | 0.09 | 0.0008 (0.001) | 0.05 | 0.58 | −0.01 (0.003) | 0.40 | <0.001 |
| $Log_{10}$(plasma NT-proBNP) | 0.13 (0.06) | 0.22 | 0.02 | −0.01 (0.05) | −0.02 | 0.82 | — | — | — |
| $Log_{10}$(plasma CNP) | −0.14 (0.12) | −0.11 | 0.24 | — | — | — | −0.06 (0.20) | −0.02 | 0.82 |
| $Log_{10}$(urinary CNP) | — | — | — | −0.09 (0.07) | −0.11 | 0.24 | 0.38 (0.16) | 0.22 | 0.02 |

$Log_{10}$ transformation was performed on plasma CNP, urinary CNP, and plasma NT-proBNP.
SE = standard error.

TABLE 7B

Multivariable Analysis of Urinary CNP, Plasma CNP, Plasma NT-proBNP in Healthy Subjects

| Predictors (Multivariable)† | $Log_{10}$(urinary CNP) β (SE) | P Value | $Log_{10}$(plasma CNP) β (SE) | P Value | $Log_{10}$(plasma NT-proBNP) β (SE) | P Value |
|---|---|---|---|---|---|---|
| Age | — | — | — | — | 0.01 (0.003) | <0.001 |
| Sex, female | 0.03 (0.02) | 0.12 | — | — | 0.07 (0.03) | 0.02 |
| eGFR | 0.005 (0.002) | 0.003 | — | — | −0.006 (0.003) | 0.03 |
| $Log_{10}$(plasma NT-proBNP) | 0.18 (0.06) | 0.005 | — | — | — | — |
| $Log_{10}$(urinary CNP) | — | — | — | — | 0.29 (0.14) | 0.04 |

$Log_{10}$ transformation was performed on urinary CNP, plasma CNP, and plasma NT-proBNP.
Predictors were selected for multivariable analysis based on a cutoff of P < 0.10 in univariable analysis (Table 7A).
†Multi variable model was not constructed for $Log_{10}$(plasma CNP); In multivariable model for $Log_{10}$(urinary CNP), $R^2$ = 0.15; In multivariable model for $Log_{10}$(plasma NT-proBNP), $R^2$ = 0.39.
SE = standard error.

TABLE 8A

Univariable Analysis of Urinary CNP, Plasma CNP, and Plasma NT-proBNP in ADHF Patients

| Predictors (Univariable) | $Log_{10}$(urinary CNP) β (SE) | r | P Value | $Log_{10}$(plasma CNP) β (SE) | r | P Value | $Log_{10}$(plasma NT-proBNP) β (SE) | r | P Value |
|---|---|---|---|---|---|---|---|---|---|
| Age | 0.005 (0.002) | 0.18 | 0.008 | 0.00002 (0.001) | 0.0002 | 0.99 | (0.003) | 0.26 | <0.001 |
| Sex, female | 0.10 (0.03) | 0.26 | <0.001 | −0.02 (0.02) | −0.05 | 0.43 | 0.04 (0.04) | 0.07 | 0.30 |
| BMI | −0.008 (0.003) | −0.19 | 0.02 | −0.05 (0.03) | −0.13 | 0.11 | −0.02 (0.005) | −0.36 | 0.001 |
| LVEF | 0.004 (0.001) | 0.29 | 0.005 | −0.002 (0.001) | −0.12 | 0.15 | −0.007 (0.002) | −0.19 | 0.03 |
| eGFR | −0.001 (0.001) | −0.07 | 0.30 | −0.003 (0.0009) | −0.20 | 0.003 | −0.01 (0.001) | −0.46 | <0.001 |
| Length of Hospital Stay | 0.001 (0.002) | 0.05 | 0.52 | 0.004 (0.002) | 0.18 | 0.01 | 0.003 (0.003) | 0.09 | 0.22 |
| Hypertension | −0.01 (0.03) | −0.03 | 0.72 | 0.05 (0.03) | 0.09 | 0.06 | 0.09 (0.04) | 0.15 | 0.03 |
| Diabetes | −0.02 (0.03) | −0.06 | 0.37 | −0.02 (0.02) | −0.07 | 0.34 | −0.05 (0.04) | −0.10 | 0.15 |
| Atrial fibrillation | 0.06 (0.02) | 0.16 | 0.02 | 0.04 (0.02) | 0.13 | 0.08 | 0.06 (0.04) | 0.11 | 0.11 |
| Ischemic heart disease | 0.04 (0.03) | 0.12 | 0.08 | 0.04 (0.02) | 0.13 | 0.07 | 0.07 (0.04) | 0.13 | 0.07 |
| Myocardial infarction | 0.04 (0.03) | 0.11 | 0.13 | 0.02 (0.03) | 0.06 | 0.40 | 0.13 (0.04) | 0.21 | 0.004 |
| Hyperlipidemia | −0.0009 (0.03) | −0.002 | 0.97 | 0.005 (0.02) | 0.01 | 0.85 | −0.02 (0.04) | −0.03 | 0.63 |
| Stroke | 0.12 (0.10) | 0.14 | 0.26 | 0.06 (0.06) | 0.07 | 0.29 | 0.16 (0.09) | 0.12 | 0.08 |
| ACEi or ARB | −0.001 (0.025) | −0.003 | 0.96 | −0.002 (0.02) | −0.002 | 0.94 | −0.08 (0.04) | −0.14 | 0.04 |
| Beta-blocker | 0.03 (0.03) | 0.07 | 0.32 | 0.006 (0.02) | 0.02 | 0.81 | −0.03 (0.04) | −0.06 | 0.37 |
| Loop diuretic | 0.09 (0.07) | 0.08 | 0.23 | 0.12 (0.07) | 0.12 | 0.08 | 0.11 (0.11) | 0.07 | 0.32 |
| Statin | −0.05 (0.02) | −0.14 | 0.05 | 0.02 (0.02) | 0.06 | 0.39 | −0.01 (0.04) | −0.03 | 0.71 |
| $Log_{10}$(plasma NT-proBNP) | 0.16 (0.05) | 0.23 | <0.001 | 0.28 (0.04) | 0.49 | <0.001 | — | — | — |
| $Log_{10}$(plasma CNP) | 0.05 (0.08) | 0.05 | 0.52 | — | — | — | 0.70 (0.10) | 0.44 | <0.001 |
| $Log_{10}$urinary CNP | — | — | — | 0.04 (0.06) | 0.05 | 0.52 | 0.34 | 0.23 | <0.001 |

$Log_{10}$ transformation was performed on urinary CNP, plasma CNP, and plasma NT-proBNP.
SE = standard error.

TABLE 8B

| Predictors (Multivariable)† | Log$_{10}$(urinary CNP) β (SE) | Log$_{10}$(urinary CNP) P Value | Log$_{10}$(plasma CNP) β (SE) | Log$_{10}$(plasma CNP) P Value | Log$_{10}$(plasma NT-proBNP) β (SE) | Log$_{10}$(plasma NT-proBNP) P Value |
|---|---|---|---|---|---|---|
| Multivariable Analysis of Urinary CNP, Plasma CNP, and Plasma NT-proBNP in ADHF Patients | | | | | | |
| Age | −0.0002 (0.002) | 0.85 | — | — | 0.003 (0.003) | 0.34 |
| Sex, female | 0.09 (0.03) | 0.005 | — | — | — | — |
| BMI | −0.002 (0.003) | 0.49 | — | — | −0.01 (0.004) | 0.02 |
| LVEF | 0.004 (0.002) | 0.02 | — | — | −0.007 (0.002) | 0.002 |
| eGFR | — | — | 0.00003 (0.001) | 0.97 | −0.004 (0.002) | 0.01 |
| Length of Hospital Stay | — | — | 0.003 (0.001) | 0.04 | — | — |
| Hypertension | — | — | 0.03 (0.02) | 0.30 | 0.01 (0.04) | 0.79 |
| Atrial fibrillation | 0.05 (0.03) | 0.05 | 0.02 (0.02) | 0.32 | — | — |
| Ischemic heart disease | 0.03 (0.03) | 0.31 | 0.02 (0.02) | 0.49 | −0.02 (0.04) | 0.61 |
| Myocardial infarction | — | — | — | — | 0.05 (0.04) | 0.30 |
| Stroke | — | — | — | — | 0.02 (0.08) | 0.81 |
| ACEi or ARB | — | — | — | — | −0.07 (0.04) | 0.07 |
| Loop diuretic | — | — | 0.05 (0.02) | 0.42 | — | — |
| Statin | −0.02 (0.03) | 0.46 | — | — | — | — |
| Log$_{10}$(plasma NT-proBNP) | 0.19 (0.06) | 0.002 | 0.25 (0.05) | <0.001 | — | — |
| Log$_{10}$(plasma CNP) | — | — | — | — | 0.44 (0.11) | <0.001 |
| Log$_{10}$(urinary CNP) | — | — | — | — | 0.35 (0.10) | 0.0008 |

Log$_{10}$ transformation was performed on urinary CNP, plasma CNP, and plasma NT-proBNP.
Predictors were selected for multivariable analysis based on a cutoff of P < 0.10 in univariable analysis (Table 8A).
†In multivariable model for Log$_{10}$(urinary CNP), R$^2$ = 0.25; In multivariable model for Log$_{10}$(plasma CNP), R$^2$ = 0.23; In multivariable model for Log$_{10}$(plasma NT-proBNP), R$^2$ = 0.45.
SE = standard error.

TABLE 9

Contemporary Normal Values for Plasma and Urinary CNP 30

| Variable | n | Median (IQR) | 95th percentile |
|---|---|---|---|
| Plasma CNP (pg/mL) | 109 | 11.8 (9.5, 15.0) | 24.7 |
| Urinary CNP (ng/g Cr) | 109 | 15.8 (12.1, 20.2) | 33.1 |

The 95% normal values for plasma and urinary CNP in healthy subjects. 35
IQR = interquartile range; CNP = C-type natriuretic peptide; Cr = creatinine.

TABLE 10

ADHF Patient Clinical Characteristics Grouped by Plasma and Urinary CNP Levels

| Variable | Normal uCNP Normal pCNP (n = 51) | Normal uCNP Elevated pCNP (n = 19) | Elevated uCNP Normal pCNP (n = 91) | Elevated uCNP Elevated pCNP (n = 47) | P value | Adjusted P value† |
|---|---|---|---|---|---|---|
| Age, years | 66 ± 12 | 67 ± 15 | 68 ± 13 | 73 ± 13 | 0.04 | 0.06 |
| Sex, female (%) | 20% | 21% | 40% | 34% | 0.07 | 0.10 |
| BMI, kg/m$^2$ | 34 ± 9 | 33 ± 9 | 32 ± 8 | 29 ± 9 | 0.05 | 0.14 |
| LVEF, % | 32 ± 15 | 30 ± 15 | 42 ± 18 | 35 ± 18 | 0.002 | 0.01 |
| eGFR, mL/min/1.73 m$^2$ | 64 ± 27 | 52 ± 21 | 60 ± 24 | 49 ± 21 | 0.10 | 0.05 |
| Length of hospital stay, days | 6 (4, 9) | 6 (3, 12) | 5 (3, 8) | 7 (4, 17) | 0.16 | 0.005 |
| Comorbidities | | | | | | |
| Hypertension, n (%) | 37 (76%) | 16 (84%) | 59 (65%) | 37 (79%) | 0.16 | 0.18 |
| Diabetes, n (%) | 17 (35%) | 8 (42%) | 42 (46%) | 12 (26%) | 0.11 | 0.10 |
| Atrial fibrillation, n (%) | 21 (43%) | 11 (58%) | 58 (64%) | 35 (74%) | 0.01 | 0.02 |
| Ischemic heart disease, n (%) | 27 (55%) | 12 (63%) | 57 (63%) | 33 (70%) | 0.50 | 0.63 |
| Myocardial infarction, n (%) | 11 (22%) | 4 (21%) | 18 (20%) | 14 (30%) | 0.61 | 0.76 |
| Hyperlipidemia, n (%) | 32 (65%) | 14 (74%) | 57 (63%) | 33 (70%) | 0.72 | 0.84 |
| Stroke, n (%) | 1 (2%) | 1 (5%) | 3 (3%) | 4 (9%) | 0.41 | 0.59 |
| Medications | | | | | | |
| ACEi or ARB, n (%) | 32 (65%) | 14 (74%) | 57 (63%) | 33 (70%) | 0.70 | 0.81 |
| Beta-blocker, n (%) | 35 (69%) | 12 (63%) | 57 (63%) | 30 (64%) | 0.62 | 0.84 |
| Loop diuretic, n (%) | 47 (92%) | 19 (100%) | 89 (98%) | 47 (100%) | 0.09 | 0.51 |
| Statin, n (%) | 34 (67%) | 12 (63%) | 48 (53%) | 30 (64%) | 0.35 | 0.65 |
| Plasma variables | | | | | | |
| NT-proBNP, pg/mL | 1589 (647, 2999) | 4457 (1942, 9869) | 2301 (1292, 5407) | 7441 (3462, 14029) | <0.001 | <0.001 |
| CNP, pg/mL | 11.3 (7.8, 16.3) | 37.5 (31.9, 78.9) | 15.4 (9.6, 19.1) | 35.7 (30.1, 48.9) | <0.001 | <0.001 |

TABLE 10-continued

ADHF Patient Clinical Characteristics Grouped by Plasma and Urinary CNP Levels

| Variable | Normal uCNP Normal pCNP (n = 51) | | Normal uCNP Elevated pCNP (n = 19) | | Elevated uCNP Normal pCNP (n = 91) | | Elevated uCNP Elevated pCNP (n = 47) | | P value | Adjusted P value† |
|---|---|---|---|---|---|---|---|---|---|---|
| Urinary variables | | | | | | | | | | |
| CNP, ng/g Cr | 24.5 | (20.2, 28.1) | 25.0 | (19.5, 28.0) | 55.8 | (43.5, 99.5) | 62.6 | (42.0, 114.6) | <0.001 | <0.001 |
| Protein, mg/mg Cr | 0.04 | (0.02, 0.08) | 0.06 | (0.02, 0.09) | 0.06 | (0.03, 0.12) | 0.08 | (0.03, 0.16) | 0.03 | 0.23 |
| Creatinine (Cr), mg/dl | 62 | (41, 84) | 50 | (32, 64) | 37 | (24, 60) | 37 | (22, 77) | 0.002 | |

Values are presented as mean ± SD, n (%), or median (interquartile range).
†Age and sex adjusted.
pCNP = plasma CNP; uCNP = urinary CNP.

TABLE 11

Predictive Values of Plasma and Urinary CNP Levels for Clinical Outcomes in ADHF Patients

| | Outcome | | | | | |
|---|---|---|---|---|---|---|
| | Rehospitalization/Death | | Rehospitalization | | Death | |
| Model | HR(95% CI) | P value | HR(95% CI) | P value | HR(95% CI) | P value |
| Normal plasma CNP/Normal urinary CNP | reference | | | | | |
| Elevated plasma CNP/Normal urinary CNP | | | | | | |
| Unadjusted | 1.76(0.98, 3.15) | 0.06 | 1.75(0.90, 3.38) | 0.10 | 1.80(0.84, 3.82) | 0.13 |
| Model 1 | 1.65(0.92, 2.97) | 0.21 | 1.69(0.87, 3.30) | 0.12 | 1.56(0.73, 3.34) | 0.25 |
| Model 2 | 1.67(0.92, 3.03) | 0.09 | 1.72(0.88, 3.38) | 0.12 | 1.64(0.76, 3.55) | 0.21 |
| Model 3 | 1.61(0.87, 2.98) | 0.13 | 1.72(0.85, 3.46) | 0.26 | 1.25(0.55, 2.86) | 0.60 |
| Normal plasma CNP/Elevated urinary CNP | | | | | | |
| Unadjusted | 1.46(0.99, 2.14) | 0.05 | 1.42(0.90. 2.22) | 0.13 | 1.57(0.94, 2.62) | 0.08 |
| Model 1 | 1.46(0.98, 2.19) | 0.07 | 1.50(0.92, 2.44) | 0.10 | 1.46(0.86, 2.47) | 0.16 |
| Model 2 | 1.44(0.96, 2.17) | 0.08 | 1.47(0.90, 2.40) | 0.12 | 1.46(0.86, 2.48) | 0.17 |
| Model 3 | 1.41(0.93, 2.15) | 0.13 | 1.49(0.89, 2.48) | 0.13 | 1.29(0.74, 2.23) | 0.37 |
| Elevated plasma CNP/Elevated urinary CNP | | | | | | |
| Unadjusted | 1.91(1.24, 2.94) | 0.004 | 1.97(1.19, 3.27) | 0.009 | 2.08(1.20, 3.10) | 0.009 |
| Model 1 | 1.77(1.11, 2.81) | 0.02 | 1.92(1.11, 3.33) | 0.02 | 1.55(0.88, 2.72) | 0.13 |
| Model 2 | 1.77(1.11, 2.83) | 0.02 | 1.92(1.10, 3.34) | 0.02 | 1.60(0.90, 2.82) | 0.11 |
| Model 3 | 1.79(1.07, 3.02) | 0.03 | 2.16(1.16, 4.03) | 0.01 | 1.26(0.66, 2.38) | 0.49 |

Unadjusted and adjusted proportional hazards regression analysis. Model 1, adjusted for age and gender; Model 2, adjusted for age, sex, eGFR, urinary protein/creatinine ratio and LVEF; Model 3, adjusted for age, sex, eGFR, urinary protein/creatinine ratio, LVEF and plasma NT-proBNP.
pCNP = plasma CNP; uCNP = urinary CNP; HR = hazard ratio; CI = confidence interval.

TABLE 12

Reclassification Analyses for Prognostic Value of Urinary and Plasma CNP Levels for Clinical Outcomes in ADHF Patients

| Model | C-statistic | IDI (95% CI) | Relative IDI (95% CI) | P value |
|---|---|---|---|---|
| Rehospitalization/ Death | | | | |
| Base model | 0.59 (0.54, 0.63) | | | |
| Base model + uCNP/pCNP groups | 0.60 (0.56, 0.65) | 0.028 (0.003, 0.079)* | 46.5% (0.2%, 174.0%)* | 0.005* |
| Base model + NT-proBNP | 0.60 (0.55, 0.64) | | | |
| Base model + NT-proBNP + uCNP/pCNP groups | 0.61 (0.56, 0.65) | 0.022 (0.001, 0.072)# | 30.0% (0.0%, 115.0%)# | 0.01# |
| Rehospitalization | | | | |
| Base model | 0.59 (0.53, 0.64) | | | |

TABLE 12-continued

Reclassification Analyses for Prognostic Value of Urinary and Plasma CNP Levels for Clinical Outcomes in ADHF Patients

| Model | C-statistic | IDI (95% CI) | Relative IDI (95% CI) | P value |
|---|---|---|---|---|
| Base model + uCNP/pCNP groups | 0.60 (0.55, 0.65) | 0.034 (0.003, 0.095)* | 49.1% (0.2%, 185.0%)* | 0.004* |
| Base model + NT-proBNP | 0.59 (0.54, 0.65) | | | |
| Base model + NT-proBNP + uCNP/pCNP groups | 0.61 (0.55, 0.66) | 0.036 (0.004, 0.103)# | 45.8% (0.6%, 164.0%)# | 0.004# |

Base model included age, sex, eGFR, urinary protein/creatinine ratio and LVEF.
uCNP/pCNP groups, the 4 subgroups based on urinary and plasma CNP levels as indicated in Table 10 and Table 11.
*IDI analyses compared to base model;
IDI analyses compared to base model + NT-proBNP;
the 95% CIs and P values were calculated based on 1000 bootstrap samples.
IDI = integrated discrimination index;
CI = confident interval.

Example 3—Materials and Methods cGMP Generation in HEK293 Cells Transfected with Human GC-B or GC-A Receptor In Vitro: HEK293 cells were stably transfected with either human GC-B or GC-A (cDNA clones from Origene, Rockville, MD) using LIPO-FECTAMINE® (Invitrogen, Grand Island, NY). Receptors overexpression was verified with immunofluorescence and western blotting. GC-B/-A transfected HEK293 cells were maintained in Dulbecco's modified Eagle's medium supplemented with 10% fetal bovine serum, 100 U/mL penicillin, 100 U/mL streptomycin, and 250 μg/mL G418. Cells were seeded in 48-well plates and cultured overnight to reach 80-90% confluency. The treatment buffer that includes, Hank's Balanced Salt Solution (HBSS) including 0.1% BSA, 2 mM HEPES and 0.5 mM 3-isobutyl-1-methylxanthine (IBMX—a non-specific phosphodiesterase inhibitor, Sigma, St. Louis, MO), was used in all experiments. HEK293 cells received treatment buffer (vehicle) only was used as a negative control and ANP ($10^{-8}$M) was used as a positive control in HEK293 GC-A cells and CNP ($10^{-8}$ M) was used as a positive control in HEK293 GC-B cells. Concentrations of CD-NP, CRRL-404, CRRL-405, CRRL-407 or CRRL=408 ($10^{-8}$, $10^{-7}$, and $10^{-6}$ M) in HBSS were incubated with HEK293 transfected GC-B or GC-A cells for 10 minutes. After treatment, all cells were washed with phosphate buffered solution (PBS) once and lysed with 0.1M HCl. Intracellular cGMP was measured in the lysate using a commercial cGMP ELISA kit (Enzo Life Sciences, Farmingdale, NY) as instructed by the manufacturer.

cGMP Generation in Human Primary Renal Cells: Human primary renal fibroblasts (HRFs, Cell Biologics, Chicago, IL) and human renal proximal tubular epithelial cells (HRPTCs, ScienCell Research Laboratories, Carlsbad, CA) were maintained and sub-cultured according to the manufacturer's protocols. Briefly, the cells were grown in 6-well plates until 80% confluency and were then treated with treatment buffer (vehicle; HBSS including 0.1% BSA, 2 mM HEPES and 0.5 mM IBMX) alone or with concentrations of CRRL-408 ($10^{-8}$, $10^{-7}$ and $10^{-6}$ M) for 10 minutes. Cells were washed with PBS once and lysed with 0.1M HCl. Intracellular cGMP was measured in the lysate using a commercial cGMP ELISA kit (Enzo Life Sciences, Farmingdale, NY) as instructed by the manufacturer described below.

cGMP Assay: The ELISA plate was coated in neutralizing solution (50 μL), prior to addition of samples and standards. Cell lysates (100 μL) and standards (100 μL), in 0.1M HCL, were incubated with cGMP conjugate (50 μL) and cGMP antibody (50 μL) at room temperature for 2 hours, 500 rpm. The plates were washed 4 times and 200 μL of pNPP substrate was added in each well and incubated for 1 hour at room temperature. The reaction was stopped by adding stop solution and absorbance was read at 405 nm and corrected for plate imperfections at 570 nm using SpectramaxM2. Standard curve was generated using the Softmaxpro software and unknown concentrations were extrapolated based on the standard curve. Samples exceeding the standard curve were diluted as needed in 0.1M HCl and corresponding dilution factors were applied to extrapolate final concentrations. The standard curve range is from 0.8 pmol/mL-500 pmol/mL. The % CV at EC50 is 6.6%.

Acute IV Infusion In Vivo Study: the cGMP generating actions of 2.12 μg/kg/minute dose CRRL-408 or vehicle (0.9% normal saline) [n=4/group] was investigated in normal rats (approximately 2 months old; 200-250 grams; Envigo, East Millstone, NJ). Studies were performed in accordance with the Animal Welfare Act and with approval of the Mayo Clinic Institutional Animal Care and Use Committee.

Rats were anesthetized with isoflurane (2-3% in oxygen) and were subjected to vessel and bladder cannulation for peptide/vehicle infusion, blood sampling and urine collection. A polyethylene (PE)-50 tube catheter was placed into the jugular vein for CRRL-408/vehicle intravenous (IV) infusion. The carotid artery was cannulated with a PE-50 tube catheter for blood sampling. The bladder was accessed and cannulated with a PE-50 tube catheter for passive urine collection. After completion of the above procedural set up, a 30 minute equilibration period was performed that included continuous IV saline infusion. After the 30 minute equilibration period the saline infusion was replaced by a continuous IV infusion (75 min including a 15 minute lead-in period) of 2.12 μg/kg/minute dose of CRRL-408 or vehicle. The infusion rate was weight adjusted and calculated as follows: rat weight (grams)*0.7/60/100 mL/minute. At the end of the 60 minute urine clearance, blood and urine were collected to determine plasma and urinary cGMP levels using a cGMP ELISA kit (Enzo Life Sciences, Farmingdale, NY) as instructed by the manufacturer.

Example 4—Results

Figure 5:
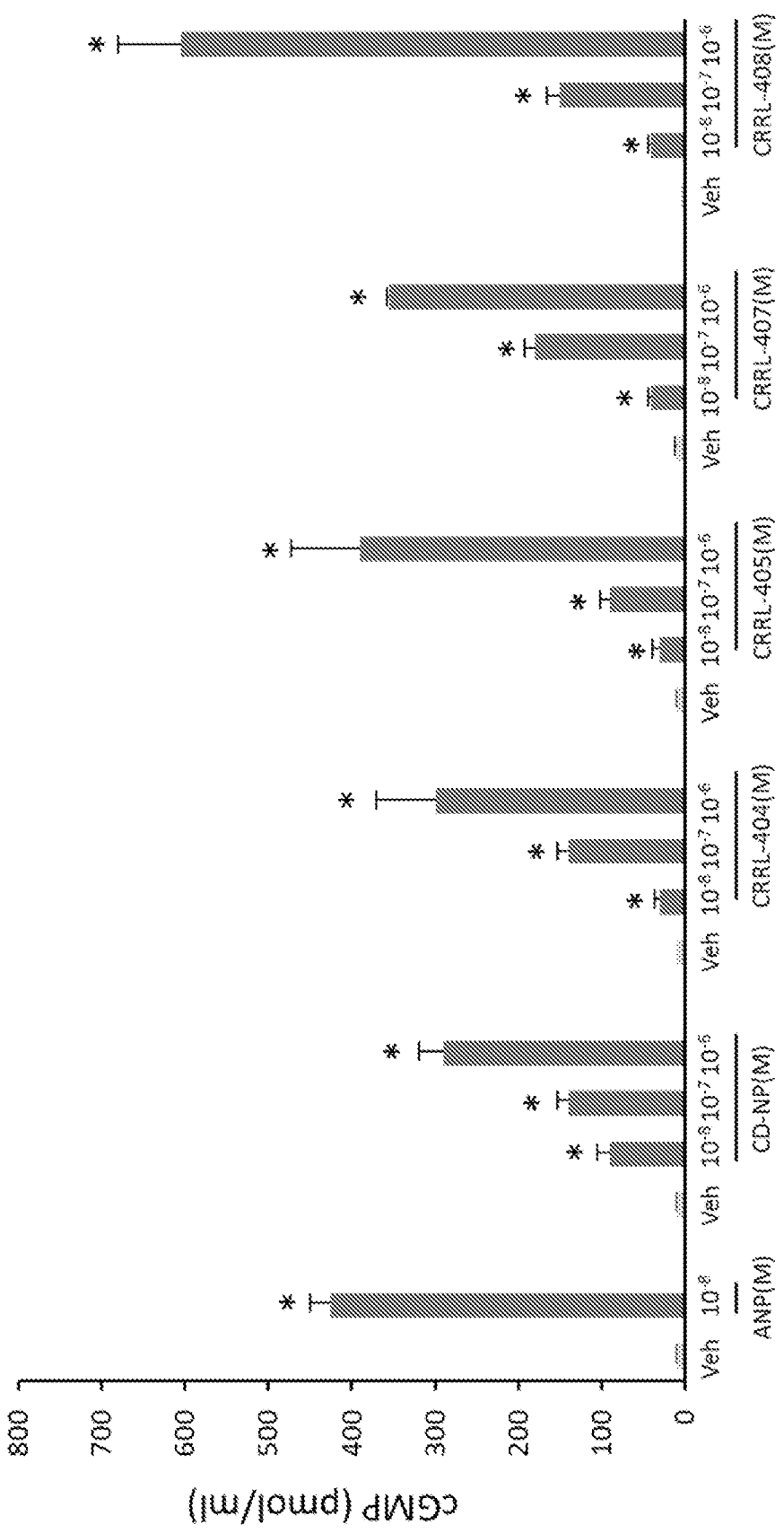
FIG. 5 is a graph plotting the level of cGMP generated in HEK293 cells overexpressing human GC-A in response to $10^{-8}$, $10^{-7}$ or $10^{-6}$ M of CD-NP, CRRL-404 (SEQ ID NO:7), CRRL-405 (SEQ ID NO:8), CRRL-407 (SEQ ID NO:9), or CRRL-408 (SEQ ID NO:10) compared to vehicle. ANP ($10^{-8}$M) was used a positive control and treatment buffer served as vehicle. *P<0.05 vs vehicle.
Figure 6:
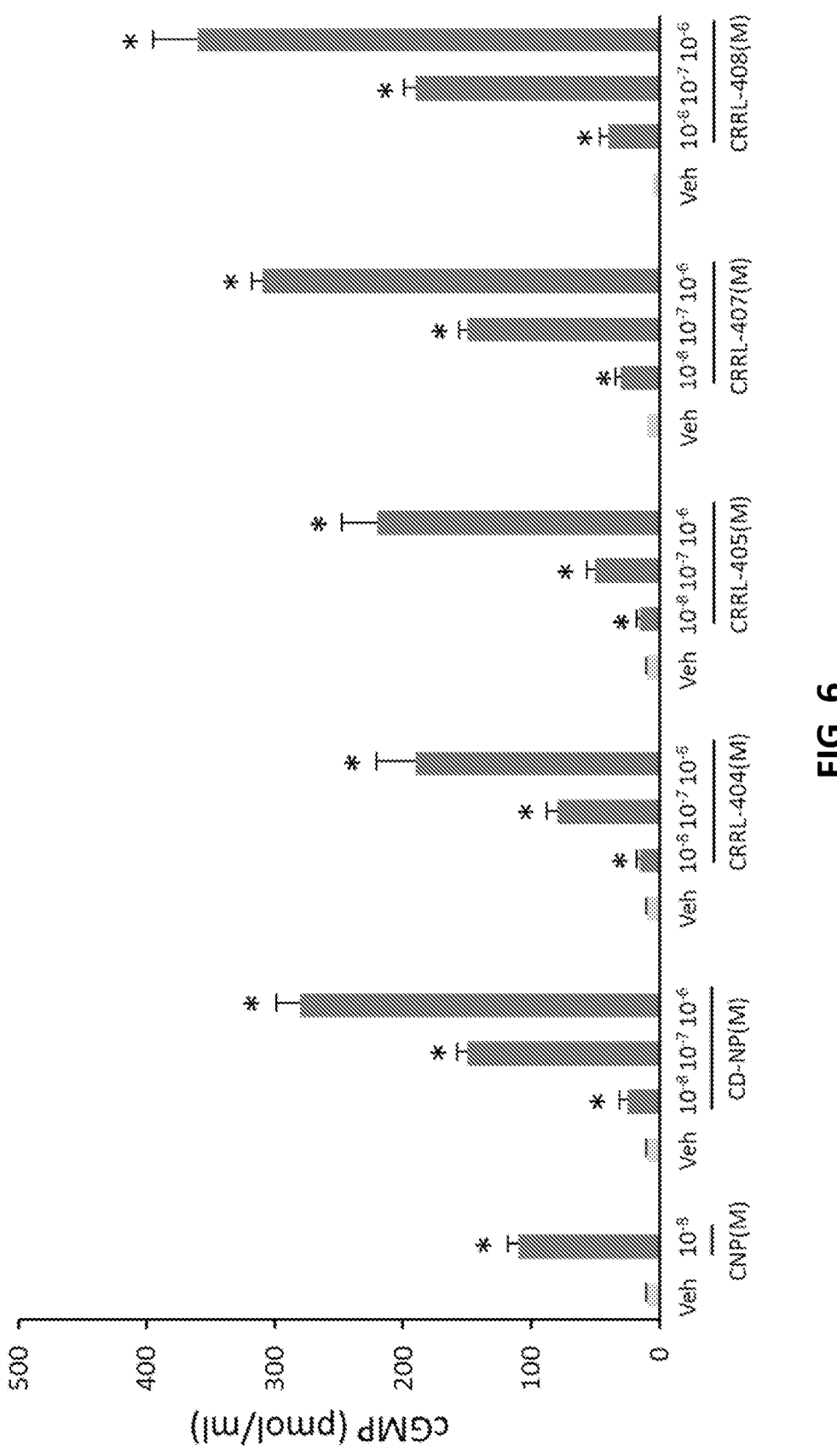
FIG. 6 is a graph plotting the level of cGMP generated in HEK293 cells overexpressing human GC-B response to $10^{-8}$, $10^{-7}$ or $10^{-6}$M of CD-NP, CRRL-404 (SEQ ID NO:7), CRRL-405 (SEQ ID NO:8), CRRL-407 (SEQ ID NO:9), or CRRL-408 (SEQ ID NO:10) compared to vehicle. CNP ($10^{-8}$M) was used a positive control and treatment buffer served as vehicle. * P<0.05 vs vehicle.

In Vitro cGMP Generation in Human GC-B or GC-A Receptor Transfected HEK293 Cells: Increasing concentrations of CD-NP, CRRL-404, CRRL-405, CRRL-407, and CRRL-408 stimulated cGMP generation in HEK293 cells overexpressing human GC-B or GC-A receptors. In particular, a dose response increase in cGMP levels of all peptide treatments was observed in HEK293 GC-A (FIG. 5) and GC-B (FIG. 6) cells, with significant cGMP generation (compared to vehicle) at all concentrations. An expected and significant cGMP generation response also was observed in HEK293 GC-A cells with ANP (FIG. 5) and in HEK293 GC-B cells with CNP (FIG. 6).

In Vitro cGMP Generation in Human Renal Fibroblasts (HRFs) and Human Renal Proximal Tubular Cells (HRPTCs): cGMP generation in HRFs and HRPTCs after exposure to CRRL-408 was investigated. These studies demonstrated that CRRL-408 increased intracellular cGMP levels in a dose dependent manner in both HRFs (FIG. 7A) and HRPTCs (FIG. 7B).

In Vivo Activity of CRRL-408 Infusion: Plasma and urinary cGMP levels were measured in rats after infusion of CRRL-408 or vehicle. Plasma cGMP (FIG. 8A) and urinary cGMP (FIG. 8B) levels were significantly elevated with CRRL-408 infusion compared to vehicle, thus demonstrating the in vivo activity of CRRL-408.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A polypeptide consisting of the amino acid sequence set forth in SEQ ID NO:7, SEQ ID NO:8, SEQ ID NO:9, or SEQ ID NO:10.

2. A composition comprising a polypeptide consisting of the amino acid sequence set forth in SEQ ID NO:7, SEQ ID NO:8, SEQ ID NO:9, or SEQ ID NO: 10.

* * * * *

SEQUENCE LISTING

<160> NUMBER OF SEQ ID NOS: 50

<210> SEQ ID NO 1
<211> LENGTH: 37
<212> TYPE: PRT
<213> ORGANISM: Artificial
<220> FEATURE:
<223> OTHER INFORMATION: synthetic polypeptide

<400> SEQUENCE: 1

Gly Leu Ser Lys Gly Cys Phe Gly Leu Lys Leu Asp Arg Ile Gly Ser
1               5                   10                  15

Met Ser Gly Leu Gly Cys Pro Ser Leu Arg Asp Pro Arg Pro Asn Ala
            20                  25                  30

Pro Ser Thr Ser Ala
        35

<210> SEQ ID NO 2
<211> LENGTH: 103
<212> TYPE: PRT
<213> ORGANISM: Homo sapiens

<400> SEQUENCE: 2

Lys Pro Gly Ala Pro Pro Lys Val Pro Arg Thr Pro Pro Ala Glu Glu
1               5                   10                  15

Leu Ala Glu Pro Gln Ala Ala Gly Gly Gly Gln Lys Lys Gly Asp Lys
            20                  25                  30

Ala Pro Gly Gly Gly Gly Ala Asn Leu Lys Gly Asp Arg Ser Arg Leu
        35                  40                  45

Leu Arg Asp Leu Arg Val Asp Thr Lys Ser Arg Ala Ala Trp Ala Arg
    50                  55                  60

Leu Leu Gln Glu His Pro Asn Ala Arg Lys Tyr Lys Gly Ala Asn Lys
65                  70                  75                  80

Lys Gly Leu Ser Lys Gly Cys Phe Gly Leu Lys Leu Asp Arg Ile Gly
                85                  90                  95

Ser Met Ser Gly Leu Gly Cys
            100

<210> SEQ ID NO 3
<211> LENGTH: 50
<212> TYPE: PRT
<213> ORGANISM: Homo sapiens

<400> SEQUENCE: 3

Lys Pro Gly Ala Pro Pro Lys Val Pro Arg Thr Pro Pro Ala Glu Glu
1               5                   10                  15

Leu Ala Glu Pro Gln Ala Ala Gly Gly Gly Gln Lys Lys Gly Asp Lys
            20                  25                  30

Ala Pro Gly Gly Gly Gly Ala Asn Leu Lys Gly Asp Arg Ser Arg Leu
        35                  40                  45

Leu Arg
    50

<210> SEQ ID NO 4
<211> LENGTH: 53
<212> TYPE: PRT
<213> ORGANISM: Homo sapiens

<400> SEQUENCE: 4

Asp Leu Arg Val Asp Thr Lys Ser Arg Ala Ala Trp Ala Arg Leu Leu

-continued

```
1               5               10              15

Gln Glu His Pro Asn Ala Arg Lys Tyr Lys Gly Ala Asn Lys Lys Gly
            20              25              30

Leu Ser Lys Gly Cys Phe Gly Leu Lys Leu Asp Arg Ile Gly Ser Met
        35              40              45

Ser Gly Leu Gly Cys
    50

<210> SEQ ID NO 5
<211> LENGTH: 31
<212> TYPE: PRT
<213> ORGANISM: Homo sapiens

<400> SEQUENCE: 5

Asp Leu Arg Val Asp Thr Lys Ser Arg Ala Ala Trp Ala Arg Leu Leu
1               5               10              15

Gln Glu His Pro Asn Ala Arg Lys Tyr Lys Gly Ala Asn Lys Lys
            20              25              30

<210> SEQ ID NO 6
<211> LENGTH: 22
<212> TYPE: PRT
<213> ORGANISM: Homo sapiens

<400> SEQUENCE: 6

Gly Leu Ser Lys Gly Cys Phe Gly Leu Lys Leu Asp Arg Ile Gly Ser
1               5               10              15

Met Ser Gly Leu Gly Cys
            20

<210> SEQ ID NO 7
<211> LENGTH: 39
<212> TYPE: PRT
<213> ORGANISM: Artificial
<220> FEATURE:
<223> OTHER INFORMATION: synthetic polypeptide

<400> SEQUENCE: 7

Lys Lys Gly Leu Ser Lys Gly Cys Phe Gly Leu Lys Leu Asp Arg Ile
1               5               10              15

Gly Ser Met Ser Gly Leu Gly Cys Pro Ser Leu Arg Asp Pro Arg Pro
            20              25              30

Asn Ala Pro Ser Thr Ser Ala
        35

<210> SEQ ID NO 8
<211> LENGTH: 41
<212> TYPE: PRT
<213> ORGANISM: Artificial
<220> FEATURE:
<223> OTHER INFORMATION: synthetic polypeptide

<400> SEQUENCE: 8

Ala Asn Lys Lys Gly Leu Ser Lys Gly Cys Phe Gly Leu Lys Leu Asp
1               5               10              15

Arg Ile Gly Ser Met Ser Gly Leu Gly Cys Pro Ser Leu Arg Asp Pro
            20              25              30

Arg Pro Asn Ala Pro Ser Thr Ser Ala
        35              40

<210> SEQ ID NO 9
```

-continued

```
<211> LENGTH: 43
<212> TYPE: PRT
<213> ORGANISM: Artificial
<220> FEATURE:
<223> OTHER INFORMATION: synthetic polypeptide

<400> SEQUENCE: 9

Lys Gly Ala Asn Lys Lys Gly Leu Ser Lys Gly Cys Phe Gly Leu Lys
1               5                   10                  15

Leu Asp Arg Ile Gly Ser Met Ser Gly Leu Gly Cys Pro Ser Leu Arg
            20                  25                  30

Asp Pro Arg Pro Asn Ala Pro Ser Thr Ser Ala
        35                  40

<210> SEQ ID NO 10
<211> LENGTH: 45
<212> TYPE: PRT
<213> ORGANISM: Artificial
<220> FEATURE:
<223> OTHER INFORMATION: synthetic polypeptide

<400> SEQUENCE: 10

Lys Tyr Lys Gly Ala Asn Lys Lys Gly Leu Ser Lys Gly Cys Phe Gly
1               5                   10                  15

Leu Lys Leu Asp Arg Ile Gly Ser Met Ser Gly Leu Gly Cys Pro Ser
            20                  25                  30

Leu Arg Asp Pro Arg Pro Asn Ala Pro Ser Thr Ser Ala
        35                  40                  45

<210> SEQ ID NO 11
<211> LENGTH: 37
<212> TYPE: PRT
<213> ORGANISM: Artificial
<220> FEATURE:
<223> OTHER INFORMATION: synthetic polypeptide

<400> SEQUENCE: 11

Lys Lys Gly Leu Gly Cys Phe Gly Leu Lys Leu Asp Arg Ile Gly Ser
1               5                   10                  15

Met Ser Gly Leu Gly Cys Pro Ser Leu Arg Asp Pro Arg Pro Asn Ala
            20                  25                  30

Pro Ser Thr Ser Ala
        35

<210> SEQ ID NO 12
<211> LENGTH: 38
<212> TYPE: PRT
<213> ORGANISM: Artificial
<220> FEATURE:
<223> OTHER INFORMATION: synthetic polypeptide

<400> SEQUENCE: 12

Lys Lys Gly Leu Ser Lys Gly Cys Phe Gly Leu Lys Leu Asp Arg Ile
1               5                   10                  15

Gly Ser Met Ser Gly Leu Gly Cys Ser Leu Arg Asp Pro Arg Pro Asn
            20                  25                  30

Ala Pro Ser Thr Ser Ala
        35

<210> SEQ ID NO 13
<211> LENGTH: 36
<212> TYPE: PRT
<213> ORGANISM: Artificial
```

```
<220> FEATURE:
<223> OTHER INFORMATION: synthetic polypeptide

<400> SEQUENCE: 13

Lys Lys Gly Leu Gly Cys Phe Gly Leu Lys Leu Asp Arg Ile Gly Ser
1               5                   10                  15

Met Ser Gly Leu Gly Cys Ser Leu Arg Asp Pro Arg Pro Asn Ala Pro
            20                  25                  30

Ser Thr Ser Ala
        35

<210> SEQ ID NO 14
<211> LENGTH: 39
<212> TYPE: PRT
<213> ORGANISM: Artificial
<220> FEATURE:
<223> OTHER INFORMATION: synthetic polypeptide

<400> SEQUENCE: 14

Lys Lys Gly Leu Arg Lys Gly Cys Phe Gly Leu Lys Leu Asp Arg Ile
1               5                   10                  15

Gly Ser Met Ser Gly Leu Gly Cys Pro Ser Leu Arg Asp Pro Arg Pro
            20                  25                  30

Asn Ala Pro Ser Thr Ser Ala
        35

<210> SEQ ID NO 15
<211> LENGTH: 39
<212> TYPE: PRT
<213> ORGANISM: Artificial
<220> FEATURE:
<223> OTHER INFORMATION: synthetic polypeptide

<400> SEQUENCE: 15

Lys Lys Gly Leu Asp Lys Gly Cys Phe Gly Leu Lys Leu Asp Arg Ile
1               5                   10                  15

Gly Ser Met Ser Gly Leu Gly Cys Pro Ser Leu Arg Asp Pro Arg Pro
            20                  25                  30

Asn Ala Pro Ser Thr Ser Ala
        35

<210> SEQ ID NO 16
<211> LENGTH: 39
<212> TYPE: PRT
<213> ORGANISM: Artificial
<220> FEATURE:
<223> OTHER INFORMATION: synthetic polypeptide

<400> SEQUENCE: 16

Lys Lys Gly Leu Ser Asp Gly Cys Phe Gly Leu Lys Leu Asp Arg Ile
1               5                   10                  15

Gly Ser Met Ser Gly Leu Gly Cys Pro Ser Leu Arg Asp Pro Arg Pro
            20                  25                  30

Asn Ala Pro Ser Thr Ser Ala
        35

<210> SEQ ID NO 17
<211> LENGTH: 39
<212> TYPE: PRT
<213> ORGANISM: Artificial
<220> FEATURE:
<223> OTHER INFORMATION: synthetic polypeptide
```

```
<400> SEQUENCE: 17

Lys Lys Gly Leu Ser Gly Gly Cys Phe Gly Leu Lys Leu Asp Arg Ile
1               5                   10                  15

Gly Ser Met Ser Gly Leu Gly Cys Pro Ser Leu Arg Asp Pro Arg Pro
            20                  25                  30

Asn Ala Pro Ser Thr Ser Ala
        35

<210> SEQ ID NO 18
<211> LENGTH: 39
<212> TYPE: PRT
<213> ORGANISM: Artificial
<220> FEATURE:
<223> OTHER INFORMATION: synthetic polypeptide

<400> SEQUENCE: 18

Lys Lys Gly Leu Ser Lys Gly Cys Phe Gly Leu Lys Leu Asp Arg Ile
1               5                   10                  15

Gly Ser Met Ser Gly Leu Gly Cys Pro Ser Leu Arg Asp Pro Arg Pro
            20                  25                  30

Asn Ala Pro Ser Thr Ser Ala
        35

<210> SEQ ID NO 19
<211> LENGTH: 39
<212> TYPE: PRT
<213> ORGANISM: Artificial
<220> FEATURE:
<223> OTHER INFORMATION: synthetic polypeptide

<400> SEQUENCE: 19

Lys Lys Gly Leu Ser Lys Gly Cys Phe Gly Leu Lys Leu Asp Arg Ile
1               5                   10                  15

Gly Ser Met Ser Gly Leu Gly Cys Asp Ser Leu Arg Asp Pro Arg Pro
            20                  25                  30

Asn Ala Pro Ser Thr Ser Ala
        35

<210> SEQ ID NO 20
<211> LENGTH: 39
<212> TYPE: PRT
<213> ORGANISM: Artificial
<220> FEATURE:
<223> OTHER INFORMATION: synthetic polypeptide

<400> SEQUENCE: 20

Lys Lys Gly Leu Ser Lys Gly Cys Phe Gly Leu Lys Leu Asp Arg Ile
1               5                   10                  15

Gly Ser Met Ser Gly Leu Gly Cys Ala Ser Leu Arg Asp Pro Arg Pro
            20                  25                  30

Asn Ala Pro Ser Thr Ser Ala
        35

<210> SEQ ID NO 21
<211> LENGTH: 39
<212> TYPE: PRT
<213> ORGANISM: Artificial
<220> FEATURE:
<223> OTHER INFORMATION: synthetic polypeptide

<400> SEQUENCE: 21

Ala Asn Lys Lys Gly Leu Gly Cys Phe Gly Leu Lys Leu Asp Arg Ile
```

-continued

```
1               5                    10                   15

Gly Ser Met Ser Gly Leu Gly Cys Pro Ser Leu Arg Asp Pro Arg Pro
            20                   25                   30

Asn Ala Pro Ser Thr Ser Ala
        35

<210> SEQ ID NO 22
<211> LENGTH: 40
<212> TYPE: PRT
<213> ORGANISM: Artificial
<220> FEATURE:
<223> OTHER INFORMATION: synthetic polypeptide

<400> SEQUENCE: 22

Ala Asn Lys Lys Gly Leu Ser Lys Gly Cys Phe Gly Leu Lys Leu Asp
1               5                    10                   15

Arg Ile Gly Ser Met Ser Gly Leu Gly Cys Ser Leu Arg Asp Pro Arg
            20                   25                   30

Pro Asn Ala Pro Ser Thr Ser Ala
        35                   40

<210> SEQ ID NO 23
<211> LENGTH: 38
<212> TYPE: PRT
<213> ORGANISM: Artificial
<220> FEATURE:
<223> OTHER INFORMATION: synthetic polypeptide

<400> SEQUENCE: 23

Ala Asn Lys Lys Gly Leu Gly Cys Phe Gly Leu Lys Leu Asp Arg Ile
1               5                    10                   15

Gly Ser Met Ser Gly Leu Gly Cys Ser Leu Arg Asp Pro Arg Pro Asn
            20                   25                   30

Ala Pro Ser Thr Ser Ala
        35

<210> SEQ ID NO 24
<211> LENGTH: 41
<212> TYPE: PRT
<213> ORGANISM: Artificial
<220> FEATURE:
<223> OTHER INFORMATION: synthetic polypeptide

<400> SEQUENCE: 24

Ala Asn Lys Lys Gly Leu Arg Lys Gly Cys Phe Gly Leu Lys Leu Asp
1               5                    10                   15

Arg Ile Gly Ser Met Ser Gly Leu Gly Cys Pro Ser Leu Arg Asp Pro
            20                   25                   30

Arg Pro Asn Ala Pro Ser Thr Ser Ala
        35                   40

<210> SEQ ID NO 25
<211> LENGTH: 41
<212> TYPE: PRT
<213> ORGANISM: Artificial
<220> FEATURE:
<223> OTHER INFORMATION: synthetic polypeptide

<400> SEQUENCE: 25

Ala Asn Lys Lys Gly Leu Asp Lys Gly Cys Phe Gly Leu Lys Leu Asp
1               5                    10                   15

Arg Ile Gly Ser Met Ser Gly Leu Gly Cys Pro Ser Leu Arg Asp Pro
```

-continued

```
              20                  25                  30

Arg Pro Asn Ala Pro Ser Thr Ser Ala
        35                  40

<210> SEQ ID NO 26
<211> LENGTH: 41
<212> TYPE: PRT
<213> ORGANISM: Artificial
<220> FEATURE:
<223> OTHER INFORMATION: synthetic polypeptide

<400> SEQUENCE: 26

Ala Asn Lys Lys Gly Leu Ser Asp Gly Cys Phe Gly Leu Lys Leu Asp
1               5                  10                  15

Arg Ile Gly Ser Met Ser Gly Leu Gly Cys Pro Ser Leu Arg Asp Pro
              20                  25                  30

Arg Pro Asn Ala Pro Ser Thr Ser Ala
        35                  40

<210> SEQ ID NO 27
<211> LENGTH: 41
<212> TYPE: PRT
<213> ORGANISM: Artificial
<220> FEATURE:
<223> OTHER INFORMATION: synthetic polypeptide

<400> SEQUENCE: 27

Ala Asn Lys Lys Gly Leu Ser Gly Gly Cys Phe Gly Leu Lys Leu Asp
1               5                  10                  15

Arg Ile Gly Ser Met Ser Gly Leu Gly Cys Pro Ser Leu Arg Asp Pro
              20                  25                  30

Arg Pro Asn Ala Pro Ser Thr Ser Ala
        35                  40

<210> SEQ ID NO 28
<211> LENGTH: 41
<212> TYPE: PRT
<213> ORGANISM: Artificial
<220> FEATURE:
<223> OTHER INFORMATION: synthetic polypeptide

<400> SEQUENCE: 28

Ala Asn Lys Lys Gly Leu Ser Lys Gly Cys Phe Gly Leu Lys Leu Asp
1               5                  10                  15

Arg Ile Gly Ser Met Ser Gly Leu Gly Cys Pro Ser Leu Arg Asp Pro
              20                  25                  30

Arg Pro Asn Ala Pro Ser Thr Ser Ala
        35                  40

<210> SEQ ID NO 29
<211> LENGTH: 41
<212> TYPE: PRT
<213> ORGANISM: Artificial
<220> FEATURE:
<223> OTHER INFORMATION: synthetic polypeptide

<400> SEQUENCE: 29

Ala Asn Lys Lys Gly Leu Ser Lys Gly Cys Phe Gly Leu Lys Leu Asp
1               5                  10                  15

Arg Ile Gly Ser Met Ser Gly Leu Gly Cys Asp Ser Leu Arg Asp Pro
              20                  25                  30

Arg Pro Asn Ala Pro Ser Thr Ser Ala
```

```
               35                   40
```

```
<210> SEQ ID NO 30
<211> LENGTH: 41
<212> TYPE: PRT
<213> ORGANISM: Artificial
<220> FEATURE:
<223> OTHER INFORMATION: synthetic polypeptide

<400> SEQUENCE: 30

Ala Asn Lys Lys Gly Leu Ser Lys Gly Cys Phe Gly Leu Lys Leu Asp
1               5                   10                  15

Arg Ile Gly Ser Met Ser Gly Leu Gly Cys Ala Ser Leu Arg Asp Pro
            20                  25                  30

Arg Pro Asn Ala Pro Ser Thr Ser Ala
        35                  40

<210> SEQ ID NO 31
<211> LENGTH: 41
<212> TYPE: PRT
<213> ORGANISM: Artificial
<220> FEATURE:
<223> OTHER INFORMATION: synthetic polypeptide

<400> SEQUENCE: 31

Lys Gly Ala Asn Lys Lys Gly Leu Gly Cys Phe Gly Leu Lys Leu Asp
1               5                   10                  15

Arg Ile Gly Ser Met Ser Gly Leu Gly Cys Pro Ser Leu Arg Asp Pro
            20                  25                  30

Arg Pro Asn Ala Pro Ser Thr Ser Ala
        35                  40

<210> SEQ ID NO 32
<211> LENGTH: 42
<212> TYPE: PRT
<213> ORGANISM: Artificial
<220> FEATURE:
<223> OTHER INFORMATION: synthetic polypeptide

<400> SEQUENCE: 32

Lys Gly Ala Asn Lys Lys Gly Leu Ser Lys Gly Cys Phe Gly Leu Lys
1               5                   10                  15

Leu Asp Arg Ile Gly Ser Met Ser Gly Leu Gly Cys Ser Leu Arg Asp
            20                  25                  30

Pro Arg Pro Asn Ala Pro Ser Thr Ser Ala
        35                  40

<210> SEQ ID NO 33
<211> LENGTH: 40
<212> TYPE: PRT
<213> ORGANISM: Artificial
<220> FEATURE:
<223> OTHER INFORMATION: synthetic polypeptide

<400> SEQUENCE: 33

Lys Gly Ala Asn Lys Lys Gly Leu Gly Cys Phe Gly Leu Lys Leu Asp
1               5                   10                  15

Arg Ile Gly Ser Met Ser Gly Leu Gly Cys Ser Leu Arg Asp Pro Arg
            20                  25                  30

Pro Asn Ala Pro Ser Thr Ser Ala
        35                  40
```

```
<210> SEQ ID NO 34
<211> LENGTH: 43
<212> TYPE: PRT
<213> ORGANISM: Artificial
<220> FEATURE:
<223> OTHER INFORMATION: synthetic polypeptide

<400> SEQUENCE: 34

Lys Gly Ala Asn Lys Lys Gly Leu Arg Lys Gly Cys Phe Gly Leu Lys
1               5                   10                  15

Leu Asp Arg Ile Gly Ser Met Ser Gly Leu Gly Cys Pro Ser Leu Arg
            20                  25                  30

Asp Pro Arg Pro Asn Ala Pro Ser Thr Ser Ala
        35                  40

<210> SEQ ID NO 35
<211> LENGTH: 43
<212> TYPE: PRT
<213> ORGANISM: Artificial
<220> FEATURE:
<223> OTHER INFORMATION: synthetic polypeptide

<400> SEQUENCE: 35

Lys Gly Ala Asn Lys Lys Gly Leu Asp Lys Gly Cys Phe Gly Leu Lys
1               5                   10                  15

Leu Asp Arg Ile Gly Ser Met Ser Gly Leu Gly Cys Pro Ser Leu Arg
            20                  25                  30

Asp Pro Arg Pro Asn Ala Pro Ser Thr Ser Ala
        35                  40

<210> SEQ ID NO 36
<211> LENGTH: 43
<212> TYPE: PRT
<213> ORGANISM: Artificial
<220> FEATURE:
<223> OTHER INFORMATION: synthetic polypeptide

<400> SEQUENCE: 36

Lys Gly Ala Asn Lys Lys Gly Leu Ser Asp Gly Cys Phe Gly Leu Lys
1               5                   10                  15

Leu Asp Arg Ile Gly Ser Met Ser Gly Leu Gly Cys Pro Ser Leu Arg
            20                  25                  30

Asp Pro Arg Pro Asn Ala Pro Ser Thr Ser Ala
        35                  40

<210> SEQ ID NO 37
<211> LENGTH: 43
<212> TYPE: PRT
<213> ORGANISM: Artificial
<220> FEATURE:
<223> OTHER INFORMATION: synthetic polypeptide

<400> SEQUENCE: 37

Lys Gly Ala Asn Lys Lys Gly Leu Ser Gly Gly Cys Phe Gly Leu Lys
1               5                   10                  15

Leu Asp Arg Ile Gly Ser Met Ser Gly Leu Gly Cys Pro Ser Leu Arg
            20                  25                  30

Asp Pro Arg Pro Asn Ala Pro Ser Thr Ser Ala
        35                  40

<210> SEQ ID NO 38
<211> LENGTH: 43
<212> TYPE: PRT
```

<213> ORGANISM: Artificial
<220> FEATURE:
<223> OTHER INFORMATION: synthetic polypeptide

<400> SEQUENCE: 38

Lys Gly Ala Asn Lys Lys Gly Leu Ser Lys Gly Cys Phe Gly Leu Lys
1               5                   10                  15

Leu Asp Arg Ile Gly Ser Met Ser Gly Leu Gly Cys Pro Ser Leu Arg
            20                  25                  30

Asp Pro Arg Pro Asn Ala Pro Ser Thr Ser Ala
        35                  40

<210> SEQ ID NO 39
<211> LENGTH: 43
<212> TYPE: PRT
<213> ORGANISM: Artificial
<220> FEATURE:
<223> OTHER INFORMATION: synthetic polypeptide

<400> SEQUENCE: 39

Lys Gly Ala Asn Lys Lys Gly Leu Ser Lys Gly Cys Phe Gly Leu Lys
1               5                   10                  15

Leu Asp Arg Ile Gly Ser Met Ser Gly Leu Gly Cys Asp Ser Leu Arg
            20                  25                  30

Asp Pro Arg Pro Asn Ala Pro Ser Thr Ser Ala
        35                  40

<210> SEQ ID NO 40
<211> LENGTH: 43
<212> TYPE: PRT
<213> ORGANISM: Artificial
<220> FEATURE:
<223> OTHER INFORMATION: synthetic polypeptide

<400> SEQUENCE: 40

Lys Gly Ala Asn Lys Lys Gly Leu Ser Lys Gly Cys Phe Gly Leu Lys
1               5                   10                  15

Leu Asp Arg Ile Gly Ser Met Ser Gly Leu Gly Cys Ala Ser Leu Arg
            20                  25                  30

Asp Pro Arg Pro Asn Ala Pro Ser Thr Ser Ala
        35                  40

<210> SEQ ID NO 41
<211> LENGTH: 47
<212> TYPE: PRT
<213> ORGANISM: Artificial
<220> FEATURE:
<223> OTHER INFORMATION: synthetic polypeptide

<400> SEQUENCE: 41

Ala Arg Lys Tyr Lys Gly Ala Asn Lys Lys Gly Leu Ser Lys Gly Cys
1               5                   10                  15

Phe Gly Leu Lys Leu Asp Arg Ile Gly Ser Met Ser Gly Leu Gly Cys
            20                  25                  30

Pro Ser Leu Arg Asp Pro Arg Pro Asn Ala Pro Ser Thr Ser Ala
        35                  40                  45

<210> SEQ ID NO 42
<211> LENGTH: 49
<212> TYPE: PRT
<213> ORGANISM: Artificial
<220> FEATURE:
<223> OTHER INFORMATION: synthetic polypeptide

<400> SEQUENCE: 42

```
Pro Asn Ala Arg Lys Tyr Lys Gly Ala Asn Lys Lys Gly Leu Ser Lys
1               5                   10                  15

Gly Cys Phe Gly Leu Lys Leu Asp Arg Ile Gly Ser Met Ser Gly Leu
            20                  25                  30

Gly Cys Pro Ser Leu Arg Asp Pro Arg Pro Asn Ala Pro Ser Thr Ser
        35                  40                  45

Ala
```

<210> SEQ ID NO 43
<211> LENGTH: 51
<212> TYPE: PRT
<213> ORGANISM: Artificial
<220> FEATURE:
<223> OTHER INFORMATION: synthetic polypeptide

<400> SEQUENCE: 43

```
Glu His Pro Asn Ala Arg Lys Tyr Lys Gly Ala Asn Lys Lys Gly Leu
1               5                   10                  15

Ser Lys Gly Cys Phe Gly Leu Lys Leu Asp Arg Ile Gly Ser Met Ser
            20                  25                  30

Gly Leu Gly Cys Pro Ser Leu Arg Asp Pro Arg Pro Asn Ala Pro Ser
        35                  40                  45

Thr Ser Ala
    50
```

<210> SEQ ID NO 44
<211> LENGTH: 53
<212> TYPE: PRT
<213> ORGANISM: Artificial
<220> FEATURE:
<223> OTHER INFORMATION: synthetic polypeptide

<400> SEQUENCE: 44

```
Leu Gln Glu His Pro Asn Ala Arg Lys Tyr Lys Gly Ala Asn Lys Lys
1               5                   10                  15

Gly Leu Ser Lys Gly Cys Phe Gly Leu Lys Leu Asp Arg Ile Gly Ser
            20                  25                  30

Met Ser Gly Leu Gly Cys Pro Ser Leu Arg Asp Pro Arg Pro Asn Ala
        35                  40                  45

Pro Ser Thr Ser Ala
    50
```

<210> SEQ ID NO 45
<211> LENGTH: 55
<212> TYPE: PRT
<213> ORGANISM: Artificial
<220> FEATURE:
<223> OTHER INFORMATION: synthetic polypeptide

<400> SEQUENCE: 45

```
Arg Leu Leu Gln Glu His Pro Asn Ala Arg Lys Tyr Lys Gly Ala Asn
1               5                   10                  15

Lys Lys Gly Leu Ser Lys Gly Cys Phe Gly Leu Lys Leu Asp Arg Ile
            20                  25                  30

Gly Ser Met Ser Gly Leu Gly Cys Pro Ser Leu Arg Asp Pro Arg Pro
        35                  40                  45

Asn Ala Pro Ser Thr Ser Ala
    50                  55
```

-continued

```
<210> SEQ ID NO 46
<211> LENGTH: 57
<212> TYPE: PRT
<213> ORGANISM: Artificial
<220> FEATURE:
<223> OTHER INFORMATION: synthetic polypeptide

<400> SEQUENCE: 46

Trp Ala Arg Leu Leu Gln Glu His Pro Asn Ala Arg Lys Tyr Lys Gly
1               5                   10                  15

Ala Asn Lys Lys Gly Leu Ser Lys Gly Cys Phe Gly Leu Lys Leu Asp
            20                  25                  30

Arg Ile Gly Ser Met Ser Gly Leu Gly Cys Pro Ser Leu Arg Asp Pro
        35                  40                  45

Arg Pro Asn Ala Pro Ser Thr Ser Ala
    50                  55

<210> SEQ ID NO 47
<211> LENGTH: 59
<212> TYPE: PRT
<213> ORGANISM: Artificial
<220> FEATURE:
<223> OTHER INFORMATION: synthetic polypeptide

<400> SEQUENCE: 47

Ala Ala Trp Ala Arg Leu Leu Gln Glu His Pro Asn Ala Arg Lys Tyr
1               5                   10                  15

Lys Gly Ala Asn Lys Lys Gly Leu Ser Lys Gly Cys Phe Gly Leu Lys
            20                  25                  30

Leu Asp Arg Ile Gly Ser Met Ser Gly Leu Gly Cys Pro Ser Leu Arg
        35                  40                  45

Asp Pro Arg Pro Asn Ala Pro Ser Thr Ser Ala
    50                  55

<210> SEQ ID NO 48
<211> LENGTH: 61
<212> TYPE: PRT
<213> ORGANISM: Artificial
<220> FEATURE:
<223> OTHER INFORMATION: synthetic polypeptide

<400> SEQUENCE: 48

Ser Arg Ala Ala Trp Ala Arg Leu Leu Gln Glu His Pro Asn Ala Arg
1               5                   10                  15

Lys Tyr Lys Gly Ala Asn Lys Lys Gly Leu Ser Lys Gly Cys Phe Gly
            20                  25                  30

Leu Lys Leu Asp Arg Ile Gly Ser Met Ser Gly Leu Gly Cys Pro Ser
        35                  40                  45

Leu Arg Asp Pro Arg Pro Asn Ala Pro Ser Thr Ser Ala
    50                  55                  60

<210> SEQ ID NO 49
<211> LENGTH: 63
<212> TYPE: PRT
<213> ORGANISM: Artificial
<220> FEATURE:
<223> OTHER INFORMATION: synthetic polypeptide

<400> SEQUENCE: 49

Thr Lys Ser Arg Ala Ala Trp Ala Arg Leu Leu Gln Glu His Pro Asn
1               5                   10                  15
```

```
Ala Arg Lys Tyr Lys Gly Ala Asn Lys Lys Gly Leu Ser Lys Gly Cys
            20                  25                  30

Phe Gly Leu Lys Leu Asp Arg Ile Gly Ser Met Ser Gly Leu Gly Cys
        35                  40                  45

Pro Ser Leu Arg Asp Pro Arg Pro Asn Ala Pro Ser Thr Ser Ala
    50                  55                  60

<210> SEQ ID NO 50
<211> LENGTH: 64
<212> TYPE: PRT
<213> ORGANISM: Artificial
<220> FEATURE:
<223> OTHER INFORMATION: synthetic polypeptide

<400> SEQUENCE: 50

Val Asp Thr Lys Ser Arg Ala Ala Trp Ala Arg Leu Leu Gln Glu His
1                   5                   10                  15

Pro Asn Ala Arg Lys Tyr Lys Gly Ala Asn Lys Lys Gly Leu Ser Lys
            20                  25                  30

Gly Cys Phe Gly Leu Lys Leu Asp Arg Ile Gly Ser Met Ser Gly Leu
        35                  40                  45

Gly Cys Pro Ser Leu Arg Asp Pro Arg Pro Asn Ala Pro Ser Thr Ser
    50                  55                  60
```